United States Patent
Needham

(10) Patent No.: US 6,726,925 B1
(45) Date of Patent: *Apr. 27, 2004

(54) TEMPERATURE-SENSITIVE LIPOSOMAL FORMULATION

(75) Inventor: David Needham, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/458,484

(22) Filed: Dec. 9, 1999

Related U.S. Application Data

(63) Continuation-in-part of application No. 09/099,668, filed on Jun. 18, 1998, now Pat. No. 6,200,598.

(51) Int. Cl.[7] ............................................. A61K 9/127
(52) U.S. Cl. .................... 424/450; 424/1.21; 424/9.321; 424/9.51; 424/94.3
(58) Field of Search ................ 424/450, 1.21, 424/9.321, 9.51, 94.3; 435/54; 436/829

(56) References Cited

U.S. PATENT DOCUMENTS

| | | | |
|---|---|---|---|
| 4,828,837 A | * 5/1989 | Uster | |
| 4,906,476 A | * 3/1990 | Radhakrishnan | |
| 4,921,644 A | * 5/1990 | Lau | |
| 4,921,706 A | * 5/1990 | Roberts | |
| 5,013,556 A | * 5/1991 | Woodle | |
| 5,049,389 A | * 9/1991 | Radhakrishnan | |
| 5,077,056 A | 12/1991 | Bally et al. | 424/450 |
| 5,080,904 A | 1/1992 | Iga et al. | 424/450 |
| 5,094,854 A | 3/1992 | Ogawa et al. | 424/423 |
| 5,277,913 A | 1/1994 | Thompson et al. | 424/450 |
| 5,552,156 A | * 9/1996 | Burke | |
| 5,683,715 A | * 11/1997 | Boni | |
| 5,720,976 A | 2/1998 | Kim et al. | 424/450 |
| 5,736,156 A | 4/1998 | Burke | 424/450 |
| 5,755,788 A | 5/1998 | Strauss | 623/11 |
| 5,783,566 A | 7/1998 | Mislick | 514/44 |
| 5,810,888 A | 9/1998 | Fenn | 607/154 |

FOREIGN PATENT DOCUMENTS

| | | | |
|---|---|---|---|
| WO | WO 92/22249 | 12/1992 | A61B/8/14 |
| WO | WO 94/13265 | 6/1994 | A61K/9/127 |
| WO | WO 95/08986 | 4/1995 | A61K/9/127 |

OTHER PUBLICATIONS

Hristova Macromolecules 28, pp. 7693–7699, 1995.*
Devlin, B.P. et al., *A Kinetic Study of the Polyelectrolyte–Induced Reorganization of Lipid Bilayers*, Am. Chem. Soc. Div. Polym. Chem.vol. 28, No. 2, (1987), pp. 50–51.
Discher et al.; *Polymersomes: Tough Vesicles Made from Diblock Copolymers*, Science 284:5417 1143–1146 (1999).
Gaber et al.; *Thermosensitive Sterically Stabilized Liposomes: Formulation and in Vitro Studies on Mechanism of Doxorubicin Release by Bovine Serum and Human Plasma* Pharmaceutical Research 12:14071416.
Hristova, K., et al., *Effect of Bilayer Composition On the Phase Behavior Liposomal Suspensions Containing Poly-(ethylene glycol) Lipids*, Macromolecules, vol. 28, No. 23 (1995) pp. 7693–7699.

(List continued on next page.)

Primary Examiner—Gollamudi S. Kishore
(74) Attorney, Agent, or Firm—Dechert LLP

(57) ABSTRACT

A liposome contains an active agent and has a gel-phase lipid bilayer membrane comprising phospholipid and a surface active agent. The phospholipids are the primary lipid source for the lipid bilayer membrane and the surface active agent is contained in the bilayer membrane in an amount sufficient to increase the percentage of active agent released at the phase transition temperature of the lipid bilayer, compared to that which would occur in the absence of the surface active agent. The surface active agent is present in the lipid bilayer membrane so as to not destabilize the membrane in the gel phase.

68 Claims, 10 Drawing Sheets

OTHER PUBLICATIONS

Iga et al.; *Heat-specific drug release of large unilamellar vesicle as hyperthermia-mediated targeting delivery* International J. Pharmaceutics 57:241–251.

Klopfenstein et al.; *Differential Scanning Calorimetry on Mixtures of Lecithin, Lysolecithin and Cholesterol;* Chemistry and Physics of Lipids 13:215–222 (1974).

Kono; *Temperature-sensitive liposomes: liposomes bearing poly (N-isopropylacrylamide)* Journal of Controlled Release 30; 69–75 (1994).

Liburdy et al.; *Microwave-Stimulated Drug Release from Liposomes* Radiation Research 103: 266–275 (1985).

Maruyama et al.; *Enhanced delivery of doxorubicin to tumor by long-circulating thermosensitive liposomes and local hyperthermia* Biochim Biophys. Acta. 1149:209–216 (1993).

Oku et al.; *Potential usage of thermosensitive liposomes for macromolecule delivery* Biochim. Biophys. Acta 1191:389–391 (1994).

Tomita et al.; *Temperature-sensitive release of adriamycin, an amphiphilic antitumor agent, from dipalmitoylphosphatidycholine-cholesterol liposomes* Biochim Biophys. Acta 978:185–190 (1989).

Van Echteld et al.; *Differential Miscibility Properties of Various Phosphatidylcholine/Lyshophosphatidylcholine Mixtures* Biochim Biophys Acta. 595:71–80 (1980).

Weinstein et al.; *Liposomes and Local Hyperthermia: Selective Delivery of Methotrexate to Heated Tumors* Science 204:188–191 (Apr. 1979).

Weinstein et al.; *Phase Transition Release, A New Approach to the Interaction of Proteins with Lipid Vesicles* Biochim Biophys. Acta. 647:270–284 (1981).

Yatvin et al.; *Design of Liposomes for Enhanced Local Release of Drugs by Hyperthermia* Science 202:1290–1292 (Dec. 1978).

Yatvin et al.; *Selective Delivery of Liposome-associated cis-Dichlorodiammineplatinum(II) by Heat and Its Influence on Tumor Drug Uptake and Growth* Cancer Research 41:1602–1607 (May 1981).

Bassett et al.; *Use of Temperature-Sensitive Liposomes in the Selective Delivery of Methotreaxate and Cis-Platinum Analogues to Murine Bladder Tumor* Journal of Urology 135:612–615 (1985).

International Search Report dated Nov. 24, 1999 for corresponding International application No. PCT/US99/12964.

\* cited by examiner 1, 2-Dipalmitoyl-*sn*-Glycero-3-Phosphocholine (DPPC)

1-Palmitoyl-2-Hydoxy-*sn*-Glycero-3-Phosphocholine (MPPC)

1, 2-Distearoyl-*sn*-Glycero-3-Phosphoethanolamine-N-[Poly(ethylene glycol)2000] (DSPE-PEG2000)

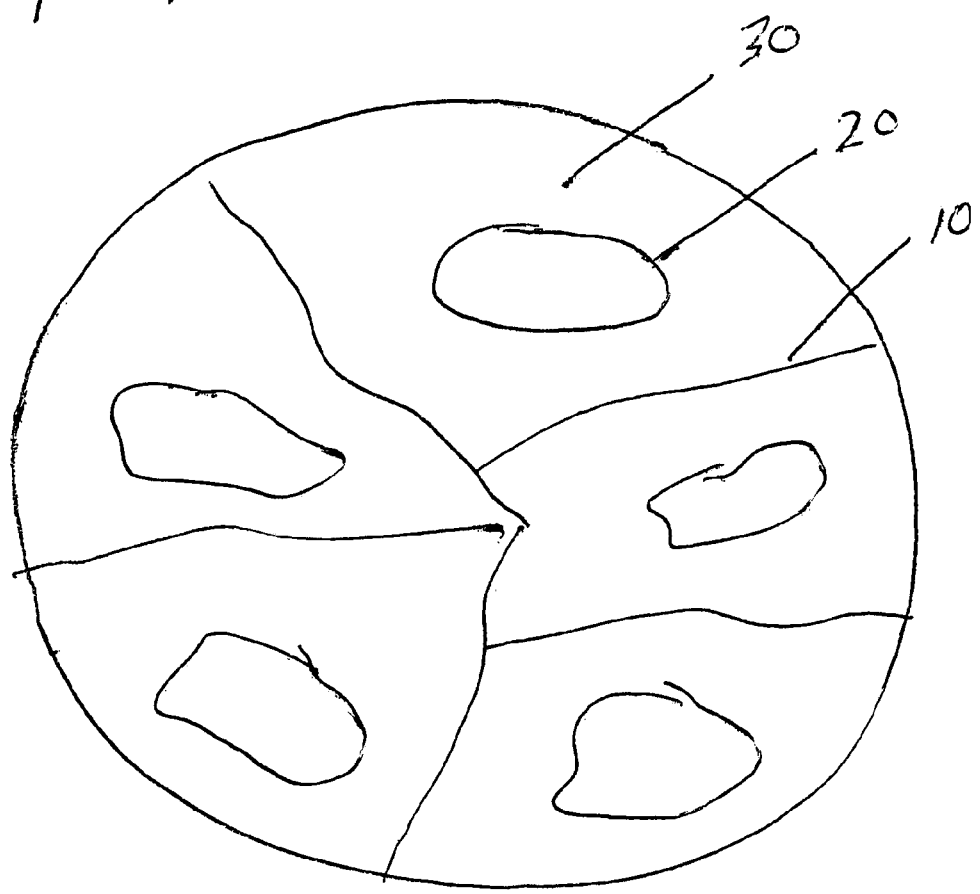

TEMPERATURE-SENSITIVE LIPOSOMAL FORMULATION

CROSS-REFERENCE TO RELATED APPLICATIONS

The instant application is a continuation-in-part application of Ser. No. 09/099,668 filed Jun. 18, 1998, now U.S. Pat. No. 6,200,598 the disclosure of which is incorporated herein by reference in its entirety.

This invention was made with Government support under National Institutes of Health grant NIH GM40162 and National Cancer Institute SPORE grant P50-CA68438. The Government may have certain rights to this invention.

FIELD OF THE INVENTION

The present invention relates to thermosensitive liposomes, and more specifically to liposomes comprising phospholipids and a surface active agent, wherein the liposomes release their contents at mild hyperthermic temperatures.

BACKGROUND OF THE INVENTION

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 $\mu$m in diameter; large unilamellar vesicles (LUVs) are typically larger than 0.05 $\mu$m. Oliglamellar large vesicles and multilamellar large vesicles have multiple, usually concentric, membrane layers and are typically larger than 0.1 $\mu$m. Liposomes with several nonconcentric membranes, i.e., several small vesicles contained within a larger vesicle, are termed multivesicular vesicles.

Conventional liposomes are formulated to carry therapeutic agents, drugs or other active agents either contained within the aqueous interior space (water soluble active agents) or partitioned into the lipid bilayer (water-insoluble active agents). Copending U.S. patent application Ser. No. 08/795,100 discloses liposomes containing cholesterol in the lipid bilayer membrane, where an active agent is aggregated with a lipid surfactant to form micelles and the micelles are entrapped in the interior space of the liposome.

Active agents that have short half-lives in the bloodstream are particularly suited to delivery via liposomes. Many anti-neoplastic agents, for example, are known to have a short half-life in the bloodstream such that their parenteral use is not feasible. These compounds also believed to distribute widely to many organs and tissues of the body to which they are toxic, thereby often limiting the concentrations that can be injected parentally. Encapsulation within liposomes typically helps to reduce this toxicity. Thus, the main goals of drug delivery are to retain drug in a biocompatible capsule thereby reducing toxicity, to avoid the body's defenses that normally recognize foreign particles and target them for removal by the liver and spleen, to instead allow targeting of the drug carrier to the therapeutic site of action, and once there, to release the drug rapidly so that it can act on the target tumor tissue. Conventional liposomes successfully achieve the first criterion, but, their use for site-specific delivery of active agents via the bloodstream is often limited by the rapid clearance of liposomes from the blood by cells of the reticuloendothelial system (RES). This problem was addressed by incorporating polyethyleneglycol lipids into the liposome membrane, that inhibits the protein adsorption that labels the liposome for RES uptake. Even if the liposomes can be made to accumulate at a diseased site such as a solid tumor, the drug is not necessarily released and available for efficacious activity; that ability to retain the drug often becomes an inhibitory factor at the tumor site.

Liposomes are normally not leaky but will become so if a hole occurs in the liposome membrane, if the membrane degrades or dissolves. Such a breakdown in permeability can be induced by the application of electric fields (electroporation), or exposure of the liposome to enzymes, or surfactants. Another, method involves raising the temperature of the membrane to temperatures in the vicinity of its gel to liquid crystalline phase transition temperature, where it appears that porous defects at phase boundary regions in the partially liquid and partially solid membrane allow the increased transport of water, ions and small molecules through the membrane. The clinical elevation of temperature in the body is called hyperthermia. This procedure has been used to raise the temperature at a target site in a subject and if temperature-sensitive liposomes can be delivered to the target site then this increase in temperature can cause the release of liposome contents, giving rise to the selective delivery of therapeutic agents, as initially described by Yatvin et al., Science 204:188 (1979). This technique is limited, however, where the phase transition temperature of the liposome is significantly higher than the normal tissue temperature.

As an example, in order to begin to use this technology for the treatment of deep-seated tumors (e.g., prostate, ovarian, colorectal and breast tumors), it is accordingly desirable to devise liposome formulations capable of delivering therapeutic amounts of active agents in response to mild hyperthermic conditions, i.e., for clinically attainable temperatures in the range 39–41° C.

SUMMARY OF THE INVENTION

In one aspect, the invention provides a liposome containing an active agent. The liposome has a solid (e.g., gel)-phase lipid bilayer membrane comprising phospholipid and a surface active agent. The phospholipids are a primary lipid source for the lipid bilayer membrane. The surface active agent is contained in the bilayer membrane in an amount sufficient to increase the percentage of active agent released at the phase transition temperature of the lipid bilayer compared to that which would occur in the absence of the surface active agent. The surface active agent is present in the lipid bilayer membrane such that the membrane is stable in the gel-phase, i.e., the presence of the surface active agent does not destabilize the membrane, particularly prior to the melting of the lipid bilayer.

In another aspect, the invention provides a liposome containing an active agent. The liposome has a gel-phase lipid bilayer membrane comprising phospholipid and a second component. Phospholipids are the primary lipid source for the lipid bilayer membrane and the second component is contained in the bilayer membrane in an amount sufficient to increase the percentage of material to be released at the phase transition temperature of the lipid bilayer compared to that which would occur in the absence of the second component. The second component is present in the lipid bilayer membrane so as to not destabilize the membrane prior to the melting of the lipid bilayer. The material to be released from the liposome is the second component or a third component which is entrapped within the liposome interior or associated with the lipid bilayer membrane.

In other aspects, the invention also provides methods for making liposomes and methods of administering liposomes as described in greater detail herein.

These and other aspects and advantages of the invention are set forth in detail hereinbelow.

BRIEF DESCRIPTION OF THE DRAWINGS

FIG. 12 shows the microboundary structure of a non-ideally mixed liposome bilayer membrane of the invention.

DETAILED DESCRIPTION OF THE INVENTION

Figure 1:
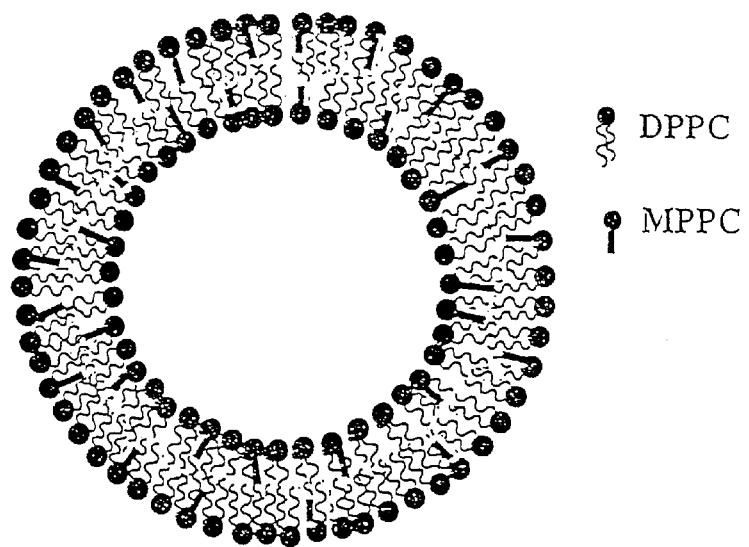
FIG. 1 schematically represents a liposome having a bilayer membrane containing dipalmitoylphosphatidylcholine (DPPC) as a phospholipid and monopalmitoylphosphatidylcholine (MPPC) as a lysolipid. The orientation of the lysolipid monomers and their presence in both the inner and outer layers of the lipid bilayer is indicated.

The present invention will now be described in reference to embodiments set forth herein and in the figures. These embodiments are merely for the purposes of illustration and are not to be interpreted as limiting the invention as defined by the claims.

The present invention provides liposomes that are sensitive to alterations in the temperature of the surrounding environment. In one aspect, the temperature-sensitivity of such liposomes allows the release of compounds entrapped within the interior aqueous space of the liposome, and/or the release of compounds associated with the lipid bilayer, at a target site that is either heated (as in the clinical procedure of hyperthermia) or that is at an intrinsically higher temperature than the rest of the body (as in inflammation). Liposome bilayers of the present invention include (in addition to a primary or main lipid component) lysolipid, or another surface active agent(s). The inclusion of lysolipid and/or other surface active agent in the liposome bilayer enhances the release of compounds when the liposome temperature reaches the gel-to-liquid crystalline phase transition temperature of the primary lipid component. In one embodiment, the presence of the lysolipid also causes the liposome to release the drug at a slightly lower temperature than that achieved with liposomes composed solely of phospholipids. This may also be effected by employing other surface active agents. As an example, liposomes of the present invention are particularly useful in drug delivery, where the liposome contains a compound to be delivered to a preselected target site in a subject's body. The target site may be either artificially heated (hyperthermia) so that it is at or above the gel-to-liquid crystalline phase transition temperature, or the target site may be at a higher temperature than non-targeted sites in the body due to natural causes (e.g., inflammation), where that temperature is at or above the gel-to-liquid crystalline phase transition temperature of the liposome utilized.

In one embodiment, when liposomes are incubated for several minutes at temperatures in the region of the gel-to-liquid crystalline phase transition temperature (Tc) of the primary lipid composing the liposome, the liposome bilayer becomes permeable and releases solutes entrapped within the liposome into the surrounding solution. The clinical use of hyperthermia with such thermally-sensitive liposomes has been proposed. See, e.g., Yatvin et al., *Science* 202:1290 (1978).

U.S. Pat. No. 5,094,854 (Ogawa et al.) discloses liposomes in which the osmotic pressure of the drug-containing solution entrapped in liposomes is 1.2–2.5 times higher than that of the body fluid of warm-blooded animals. The temperature range in which the liposome membrane becomes permeable to material release is stated to be in the range of 40° C. to 45° C.

U.S. Pat. No. 5,720,976 (Kim et al.) discloses the use of a copolymer of N-isopropylacrylamide/octadecylacrylate/acrylic acid to coat the liposomal surface to effect the release of agents contained within the liposome. Release of the entrapped agent occurs at temperatures above 28° C. (well below average human temperature). Methods of heating a subject's body for therapeutic purposes or to assist in the delivery of therapeutic or diagnostic agents are known in the art. Hyperthermia consists of heating diseased sites, such as solid tumors, to temperatures higher than the physiological temperature (e.g., from about 38° C. to about 45° C.), and is currently used mainly as an adjunct to radiation therapy (Bates and Mc Killop *Cancer Res.* 46:5477 (1986); Herman, *Cancer Res.* 43, 511 (1983)).

As used herein, the term "hyperthermia" refers to the elevation of the temperature of a subject's body, or a part of a subject's body, compared to the normal temperature of the subject. Such elevation may be the result of a natural process (such as inflammation) or artificially induced for therapeutic or diagnostic purposes. In mammals, a normal body temperature is ordinarily maintained due to the thermoregulatory center in the anterior hypothalamus, which acts to balance heat production by body tissues with heat loss. "Hyperthermia" refers to the elevation of body temperature above the hypothalamic set point due to insufficient heat dissipation. In contrast to hyperthermia, "fever" refers to an elevation of body temperature due to a change in the thermoregulatory center. The overall mean oral temperature for a healthy human aged 18–40 years is 36.8±0.4° C. (98.2±0.7° F.). See, e.g., Harrison's Principles of Internal Medicine (Fauci et al., Eds.) 14$^{th}$ Edition, McGraw-Hill, New York, p. 84 (1998).

The use of hyperthermia with thermally-sensitive liposomes has been proposed, for example, for the treatment of tumors (Yatvin et al., *Science* 202:1290 (1978)). Using localized hyperthermia and thermally-sensitive liposomes to target anti-neoplastic agents to tumor sites in a subject acts to decrease undesirable side effects of the agent, and to enhance therapeutic results. However, the efficacy of liposomes targeted to diseased sites by hyperthermia depends on the stability of the liposome in the blood stream (when liposomes are administered to the circulatory system), and on the amount of active agent released by the liposome at the target site. For example, liposomes described by Yatvin et al, *Science* 202:1290 (1978) released only a portion of the drug carried by the liposome at hyperthermic temperatures.

As used herein, "hyperthermic administration" of an active agent refers to its administration in conjunction with the use of clinical hyperthermia in the subject at a preselected target site, to deliver a larger amount of active agent to the target site compared to that which would result from the administration of the active agent in the absence of hyperthermia.

In one embodiment, liposomes of the present invention comprise a lipid possessing a gel-to-liquid crystalline transition temperature in the hyperthermic range (e.g., the range of from approximately 38° C. to approximately 45° C.). Preferred are phospholipids with a phase-transition temperature of from about 38° C. to about 45° C., and more preferred are phospholipids whose acyl groups are saturated. A particularly preferred phospholipid is dipalmitoylphosphatidylcholine (DPPC). DPPC is a common saturated chain (C16) phospholipid with a bilayer transition of 41.5° C. (Blume, *Biochemistry* 22:5436 (1983); Albon and Sturtevant, *Proc. Natl. Acad. Sci. USA* 75:2258 (1978)). Thermosensitive liposomes containing DPPC and other lipids that have a similar or higher transition temperature, and that mix ideally with DPPC (such 1, 2-Dipalmitoyl-sn-Glycero-3-[Phosphorac-(1-glycerol)] (DPPG) (Tc=41.5° C.) and 1, 2-Distearoyl-sn-Glycero-3-Phosphocholine (DSPC) (Tc=55.10° C.)) have been studied. Kastumi Iga et al, *Intl. J. Pharmaceutics*, 57:241 (1989); Bassett et al, *J. Urology*, 135:612 (1985); Gaber et al, *Pharmacol. Res.* 12:1407 (1995). Thermosensitive liposomes containing DPPC and cholesterol have also been described. Demel and De Kruyff, *Biochim. Biophys. Acta.* 457:109 (1976). Other examples of phospholipids that can be employed include di-chain phospholipids (e.g., phosphacholines) such as, but are not limited to, a C12 saturated chain phospholipid (Tc=10° C.), a C14 saturated chain phospholipid (Tc=24° C.), a C16 saturated phospholipid (Tc=41° C.), a C18 saturated phospholipid (Tc=55° C.), a C20 saturated phospholipid (Tc=65° C.), a C22 saturated phospholipid (Tc=70° C.), and a C24 saturated phospholipid (Tc=80° C.). Similarly, other common phospholipids that may be used include, but are not limited to, phosphatdyl glycerols, inositols, ethanolamines shpyngomyelins, and gangliosides that as with the phosphatidylcholines have phase transition temperatures that vary in a similar fashion dependent of their acyl chain length.

It should be appreciated that other membrane-forming materials can be used which are not phospholipids for the purposes of the invention. Exemplary materials which may form a solid-phase membrane include, but are not limtied to, bola lipids or bacterial lipids. Additionally, block copolymers comprising a water-soluble polymers (e.g., polyethylene glycol) and a water-insoluble polymer (e.g., polypropylene oxide and polyethylethylene) can be employed.

As used herein, the "primary lipid" in a liposome bilayer is that which is the main lipid component of liposome bilayer material. Thus, for example, in a liposome bilayer composed of 70 mole % phospholipid and 30 mole % lysolipid, the phospholipid is the primary lipid.

Liposomes of the present invention incorporate a relatively-water soluble surface active agent, such as, for example, a lysolipid, into a bilayer composed primarily of a relatively water-insoluble molecule, such as a di-chain phospholipid (e.g., DPPC). Incorporation of the surface active agent in the gel phase of the primary lipid component enhances the release of contents from the resulting liposome when heated to the gel-liquid crystalline phase transition temperature of the primary lipid. Preferred surface active agents are lysolipids, and a particularly preferred surface active agent is monopalmitoylphosphatidylcholine (MPPC). Other lysolipids can also be used and include, but are not limited to, monoacylphosphatydlcholines where the head group can be phosphatdyl glycerols, inositols, ethanolamines, or ceramides, and the single acyl chain can be for example C8–C22, with one or more C=C double bonds in the chain. Exemplary lysolipids include, but are not limited to, monopalmitoylphosphatidylcholine (MPPC). monolaurylphosphatidylcholine (MLPC), monomyristoylphosphatidylcholine (MMPC), monostearoylphosphatidylcholine (MSPC), and mixtures thereof.

Lysolipid basically encompasses C12–C18 monoacyl lysolipids. It should be appreciated that longer acyl chains can be included preferably if the head group is made more soluble. Moreover, other suitable surface active agents may include, for example, a dichain phospholipid having chains preferably of no greater than C10, glycolipids, and bile salts that are quite surface active but will enter a bilayer without dissolving it at concentrations less than their CMC, which can be as high as tens of milliMolar.

Suitable surface-active agents are those that are compatible with the primary lipid of the bilayer, and that desorb when the lipid melts to the liquid phase. It should also be appreciated that other surface-active agents that are not completely compatible with the primary lipid may also be employed. Additional suitable surface-active agents for use in phospholipid bilayers include, but are not limited to, palmitoyl alcohols, stearoyl alcohols, myristoyl surfactants, stearoyl surfactants, palmitoyl surfactants polyethylene glycol, glyceryl monopalmitate, glyceryl monooleate, ceramides, PEG-ceramides, and therapeutic lipids. Therapeutic lipids include, for example, C-18 ether linked lysophoshpatidylchohline. Block copolymers may be used and include, for example, polyethylene glycol-polyethylene oxide and polyethylene glycol-polyethylene copolymers. It will be appreciated by those skilled in the art that many types of surface active agents that can be used include, but are not limited to, cationic, anonic, and neutral surface active agents, such as, for example, fatty acids, glucosides, bile acids, and block copolymers.

In one embodiment, a preferred liposome of the present invention incorporates a bilayer-compatible lysolipid in a phospholipid bilayer, the lysolipid present in the bilayer at a concentration sufficient to enhance the release of contents (e.g., active agent or therapeutic agent) from the liposome, compared to the release of contents that would be achieved using a liposome composed of only lipid alone (i.e., without lysolipid). The contents may be contained within the interior of the liposome or in the liposome membrane. By "enhanced release", it is meant that either (a) that a greater percentage of contents is released at a given temperature, compared to the amount of contents released at that temperature by a liposome with a bilayer composed of phospholipid only; or (b) the contents entrapped in the interior of the liposome are released at a lower temperature than the temperature at which release of contents would occur using a lipsome with a bilayer composed of phospholipid only. It will also be appreciated that in certain embodiments, the addition of some second components may raise the temperature of the phase transition and thereby raise the temperature at which the bilayer becomes permeable above that of the phospholipid alone.

The present invention provides liposomes that release entrapped or encapsulated contents at temperatures that can be achieved in clinical settings using mild hyperthermia. For the purposes of illustration, in one example, the present invention provides liposomes that are highly stable at body temperature (37° C.) but that become unstable and show enhanced release of entrapped compounds at temperatures beyond about 39° C. This temperature range is a few degrees below that of many previous liposomal formulations that only showed significant release at temperatures greater than 42° C. Additionally, the present liposomal formulation's combination of lipid and compatible lysolipid provides a lipid/lysolipid mixture with a slightly lower gel-to-liquid crystalline transition temperature (of the lipid bilayer) compared to that of pure lipid alone, yet the gel-to-liquid crystalline transition temperature is not broadened by the inclusion of a lysolipid.

A preferred embodiment relates to a liposome having a bilayer composed primarily of phospholipid, and containing lysolipid in an amount that decreases the gel-to-liquid crystalline phase transition temperature of the bilayer, compared to a bilayer composed of phospholipid alone. A particularly preferred liposome of the present invention comprises a DPPC as the primary phospholipid and MPPC as the lysolipid, where the ratio of DPPC:MPPC is from about 99:1, 98:2, 97:3, 96:4, 95:5, 90:10, to about 80:20, 75:25, 70:30, 65:35, 60:40, or even 51:49 (by molar ratio). These ratios may apply to other phospholipids and surface active agents set forth herein.

An additional embodiment would include a monostearoylphosphatidylcholine, that raises the transition temperature above that for the pure lipid, and enhances the release of entrapped contents. This formulation, is expected to be useful for drug delivery applications in dogs where the natural body temperature is approximately 39° C. Similarly, an additional embodiment would include a monomyrstoylphosphatidylcholine, that lowers the transition temperature whilst still enhancing the release of contents compared to the pure membrane forming material alone. Such a formulation would be useful for therapies directed in cold-blooded animals where body temperature is not necessarily regulated to 37° C.

The present invention provides a new system for delivering active agents in a lipid carrier, wherein active agents are released from the carrier over a narrow temperature range. In one embodiment, local heating of target sites to mildly hyperthermic temperatures (i.e., 39° C. to 41° C.) allows preferential delivery of the active agent to a diseased site. The present liposomes are suited for use in combination with hyperthermia to target active agents to disease sites, compared to conventional liposomes that only release active agents slowly and that are not thermosensitive, or compared to thermosensitive liposomes fundamentally different compositions (dichain phospholipids and cholesterol, that do not contain, for example, a second water-soluble surfactant) and that do not release active agents until reaching temperatures of 42° C. or above.

While not wishing to be held to any single theory of action, the present inventors believe that the mechanism whereby lysolipids (or other surface active agents or active agents that may also be surface active) enhance the release of contents from liposomes in one embodiment composed primarily of phospholipid is related to the way in which the lysolipid is mostly ideally mixed in the mixed gel phase bilayer, but creates defects at the microstructural level (microdomain boundaries) as it desorbs from the membrane upon bilayer melting at the primary acyl chain transition temperature (i.e., at the transition temperature of the primary bilayer lipid/surface active agent (e.g., lysolipid) mixture). The inclusion of a surface active agent such as a lysolipid lowers the phase transition temperature of a lipid bilayer membrane, compared to the phase transition temperature of a membrane composed solely of the phospholipid. In a liposome composed of DPPC and MPPC, the phase transition temperature is lowered depending on the amount of MPPC incorporated into the gel phase bilayer; the reduction of phase transition temperature that can be achieved is limited by the amount of MPPC that can be stably contained in the bilayer. Membranes composed of phospholipid (e.g., DPPC) can stably contain from 1 mol % surface active agent (e.g., MPPC), up to about 20 mole %, 30% mole %, 40 mol %, or even 50 mol % surface active agent, depending on other conditions such as the active agent contained within the liposome.

Additionally, surface active agent and phospholipid may be present in a non-ideally mixed form in the lipid bilayer. FIG. 12 is a diagram illustrating the phases in such a system. A non-ideally mixed system contains second phase precipitates that form microdomain inter-grain boundaries 10 similar to those which are in an ideally mixed system described above as well as intra-grain boundaries 20 segregating an intra-grain region (e.g., precipitated second phase) within a given primary phase 30. The formation of and the structure of the lipid bilayer illustrated in this embodiment may be influenced by various factors such as, but not limited to, types and concentrations of bilayer components, cooling rates, and others. Not wishing to be bound by theory, the present inventors believe that the mechanism whereby surface active agents may enhance the release of contents from liposomes in this embodiment is related to the formation of defects at the microstructural level (microdomain boundaries) as it desorbs from the membrane upon bilayer melting at the primary acyl chain transition temperature (i.e., at the transition temperature of the primary bilayer lipid/surface active agent mixture). In the embodiment set forth in FIG. 12, the defects occur at the microdomain inter-grain boundaries 10 and well as the intra-grain boundaries 20. Thus, the enhanced release benefits can be realized in lipid bilayers in which phospholipid(s) and surface active agent are non-ideally mixed as well as ideally mixed.

In liposome bilayers containing phospholipid and a surface active agent such as a lysolipid, it is preferable that the surface active agent be contained in both layers of the bilayer. This concept of this embodiment is illustrated in FIG. 1, which schematically represents a liposome composed of DPPC and MPPC. The molecules of MPPC are present in both the exterior and the interior layer of the liposome membrane bilayer. In a liposome containing surface active agent in only one layer of the bilayer, redistribution of the surface active agent to both layers of the bilayer will occur over time at temperatures above the gel transition temperature (e.g., in the liquid crystalline phase).

Figure 11A:
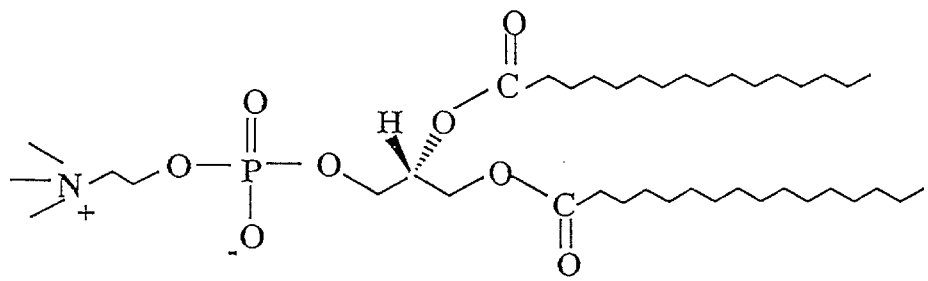
FIG. 11A shows the chemical structure of 1,2-Dipalmitoyl-sn-Glycero-3-Phosphocholine (DPPC).
Figure 11B:
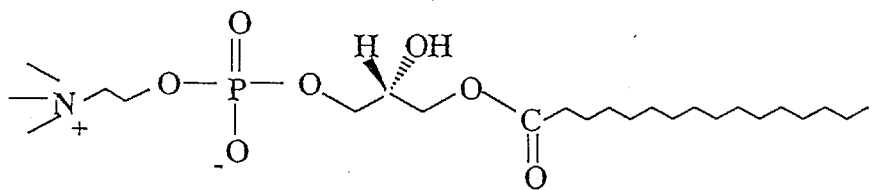
FIG. 11B shows the chemical structure of 1-Palmitoyl-2-Hydoxy-sn-Glycero-3-Phosphocholine (MPPC).

Phase compatibility of the two (or more) components of the present invention affects the processing and stability of the lipid bilayer structure. For example, in liposomes composed primarily of DPPC (a di-chain phospholipid), to maximize compatibility and preserve the narrow melting range of the main phospholipid, a preferred surface active agent is lysolipid such as MPPC because it is identical to the di-chain phospholipid except that it possesses only one acyl chain (FIGS. 11A and 11B). In one embodiment, the present inventors discovered that inclusion of this bilayer-compatible lysolipid in low concentrations (preferably 2–20 mol %), makes liposomes composed primarily of DPPC more "leaky" at the point at which the primary lipid begins to melt (i.e., the solidus line of the main phase transition), compared to liposomes composed of DPPC alone. While not wishing to be held to a single explanation, the present inventors believe that gel phase bilayers are composed of microcrystalline domains; as the temperature approaches the gel-to-liquid crystalline phase transition of the lipid bilayer, membrane permeability to the entrapped drug increases at the grain boundaries of the microstructure. At the transition temperature, desorption of the lysolipid dissolved in the gel phase microstructure enhances the membrane permeability. An additional benefit of incorporating a compatible molecule in the liposome bilayer is that the phase transition temperature of the primary lipid is not broadened, but is lowered (or raised depending on the application) by about a degree or more (depending on the lysolipid concentration in the bilayer).

In another embodiment, the invention provides a liposome having a gel-phase lipid bilayer membrane comprising phospholipid and a second component. The phospholipids are the primary lipid source for the lipid bilayer membrane. The second component is one which is capable of increasing the percentage of material to be released at the phase transition temperature compared to that which would occur in the absence of the second component. Thus, the second component is present in the lipid bilayer membrane in an amount such that it allows for this enhanced release. Additionally, the second component is present in the lipid bilayer membrane so as to not destabilize the membrane prior to the melting of the lipid bilayer, i.e., the bilayer membrane is stable in the gel-phase with surface active agent being contained therein. The material to be released may be the second component, or a third component which is entrapped within the liposome interior or associated with the lipid bilayer membrane. The third component may encompass active agents such as, but not limited to, those described herein.

The second component as set forth above encompasses a wide range of substances. In a preferred embodiment, the second component is an amphiphilic material including, but not limited to, surface active agents set forth herein. Materials that are released includes compounds described herein such as, for example, active agents (e.g., pharmaceutically active agents) entrapped within the interior aqueous space of the liposome, and/or associated with the lipid bilayer. In certain embodiments, the second component and the material that are released may be the same, i.e., the second component is entrapped within the lipid bilayer. In this instance, an example of a second component may include, but not be limited to, water-insoluble or membrane-soluble pharmaceutically active agents such as apoptotic agents (e.g., ceramides) as well as platelet activating factor. Other agents may include, common surfactants as listed above, and drugs themselves with limited water solubility that can preferentially associate with a liquid lipid membrane and that can then be trapped in the membrane when the main membrane forming lipid is cooled into the gel phase. Upon raising the temperature to the transition region, this second component that may itself be a drug is released from the membrane into the surrounding aqueous fluid. If this fluid is the bathing fluid in a tumor tissue or cell interior, then the active agent may be available for therapeutic action.

In the event that the second component is the material whose released is enhanced are the same, the liposome preferably comprises from about 1 to about 50 mol percent of the second component and more preferably from about 1 to about 30 mol percent of the second component.

Although not intending to be bound by theory, in the above-described embodiments, Applicants believe that the second component may accumulate at the microgram boundaries in the gel-phase lipid bilayer. As the bilayer melts, the second component releases or desorbs from the bilayer at these grain boundaries and thus exits the lipid bilayer in a manner described herein. Lipid bilayers that may be employed in these embodiments include systems in which the phospholipid and second component are ideally mixed or non-ideally mixed as described above.

The process of forming the mixed component liposomes of the present invention involves preparation of gel phase liposomes containing a phospholipid, an appropriate surface active agent (such as lysolipid), and the active agent of interest. Other phase compatible components such as DSPE-PEG can optionally be included, as discussed further below. The composition contains a percentage of lysolipid such that the surface active agent does not destabilize the membrane at processing temperatures where the bilayer is in the liquid phase, nor at physiological temperatures where the bilayer is in the gel phase. The bilayer becomes unstable and. permeable at temperatures in the range of the membrane phase transition, which can be made to be just above normal human body temperature, and rapidly releases entrapped material from the liposome interior.

Liposomes according to the present invention may be prepared by any of a variety of techniques that are known in the art. See, e.g., U.S. Pat. No. 4,235,871; Published PCT applications WO 96/14057; New RRC, *Liposomes: A practical approach*, IRL Press, Oxford (1990), pages 33–104; Lasic DD, *Liposomes from physics to applications*, Elsevier Science Publishers, Amsterdam, 1993; *Liposomes*, Marcel Dekker, Inc., New York (1983). Entrapment of an active agent within liposomes of the present invention may also be carried out using any conventional method in the art. In preparing liposome compositions of the present invention, stabilizers such as antioxidants and other additives may be used as long as they do not interfere with the purpose of the invention.

The amount of surface active agent (such as, for example, lysolipid) included in liposomes of the present invention is not sufficient to destabilize the membrane in the liquid phase that occurs during processing of the liposomes (prior to cooling to produce the gel phase product). In producing liposomes according to the present invention, it is preferable during processing of the liquid phase membranes to maintain a concentration of surface active agent monomer both inside and outside the liposome, to avoid a concentration gradient that would deplete the surface active agent concentration in the membrane. This can be achieved by preparing the liposomal suspension from a premixed mixture in an aqueous medium containing sufficient amount of surface active agent in monomeric form, (e.g., at approximately but not greatly exceeding the critical micelle concentration (CMC) of the surface active agent).

A method of preparing a liposomal formulation according to the present invention comprises mixing the bilayer components in the appropriate proportions in a suitable organic solvent, as is known in the art. The solvent is then evaporated to form a dried lipid film. The film is rehydrated (at temperatures above the phase transition temperature of the lipid mixture) using an aqueous solution containing an equilibrating amount of the surface active agent and a desired active agent. The liposomes formed after rehydration can be extruded to form liposomes of a desired size, as is known in the art. For example, where liposomes composed of 80:20 DPPC:MPPC are produced, rehydration is carried out at a temperature above the phase transition temperature of this particular lipid mixture (above 39° C.). The aqueous solution used to rehydrate the lipid film comprises an equilibrating amount of lysolipid monomers (e.g., a concentration equal to the Critical Micelle Concentration of MPPC, about 1 micromolar).

Conventional liposomes suffer from a relatively short half life in the blood circulation due to their rapid uptake by macrophages of the liver and spleen (organs of the reticuloendothelial system or RES), and therefore do not accumulate in leaky tumor tissue. Liposome preparations have been devised which avoid rapid RES uptake and which have increased circulation times. STEALTH® liposomes (Sequus Inc., Menlo Park, Calif.) include polyethyleneglycol (PEG)-grafted lipids at about 5 mol % in the lipid bilayer. See, e.g., Allen, *UCLA Symposium on Molecular and Cellular Biology*, 89:405 (1989); Allen et al., *Biochim. Biophys. Acta* 1066:29 (1991); Klibanov et al., *FEBS Letters* 268:235 (1990); Needham et al., *Biochim. Biophys. Acta* 1108:40 (1992); Papahadjopoulos et al., *Proc. Natl. Acad. Sci. USA* 88:11460 (1991); Wu et al., *Cancer Research* 53:3765 (1993); Klibanov and Huang, *J. Liposome Research* 2:321 (1992); Lasic and Martin, Stealth Liposomes, In: Pharmacology and Toxicology, CRC Press, Boca Raton, Fla. (1995). See also U.S. Pat. No. 5,225,212 to Martin et al.; U.S. Pat. No. 5,395,619 to Zalipsky et al. regarding liposomes containing polymer grafted lipids in the vesicle membrane. The presence of polymers on the exterior liposome surface decreases the uptake of liposomes by the organs of the RES.

Liposomes of the present invention may be formulated to include polymer-grafted lipids, as is known in the art, to decrease liposome uptake by the RES and thus increase the circulation time of the liposomes. Suitable polymers include hydrophilic polymers such as polyethylene glycol, polyvinylpyrolidine, olylactic acid, polyglycolic acid, copolymers of polylactic acid and polyglycolic acid, polyvinyl alcohols, polyvinylpyrrolidone, dextrans, oligosaccharides, along with mixtures of the above. It is believed that most current liposome drug delivery systems are composed of lipids that form liquid-phase bilayers at room or body temperatures. If one of the component lipids actually has a relatively high transition temperature, the liposomes are conventionally formed reproducibly at temperatures above this transition. It is also usual for loading of active agents to be carried out at temperatures above the phase transition of the membrane lipids, i.e., in the liquid phase of the lipid.

In view of the preceding paragraph, in another aspect the invention provides a method for loading active agents into liposomes. The method comprises providing a liposome comprising a gel-phase lipid bilayer, with the lipid bilayer comprising phospholipid. The lipid bilayer is present at a temperature below its phase transition temperature. The lipid bilayer is then exposed to an active agent such that the active agent passes into and through the lipid bilayer, entering the liposome interior. The method of loading active agents into liposomes allows for an increase in the percentage of active agent released at the phase transition temperature of the liposome membrane, compared to that which would occur in liposomes produced by another method.

The method described above may further comprise other steps. For example, the method may comprise the step of cooling the liposome to a temperature below the phase transition temperature of the lipid bilayer prior to exposing the active agent to the bilayer.

In a preferred embodiment, the liposome is present in a surrounding liquid medium, and wherein the pH of the surrounding liquid medium is greater than the pH of the interior of the liposome. This pH gradient is believed to facilitate loading of the active agent into the interior of the liposome.

Active Agents

As used herein, an active agent 'in the interior' or 'entrapped within' the liposome is that which contained in the interior space of the liposome, compared to that partitioned into the lipid bilayer and contained within the vesicle membrane itself. As used herein, an active agent 'within' or 'entrapped within' the lipid bilayer of a liposome is carried as a part of the lipid bilayer, as opposed to being contained in the interior space of the liposome. Active agents may be in any form suitable for use in liposomes, as is known in the art, including but not limited to aqueous solutions of active agents. Aqueous solutions of active agents within liposomes of the present invention may be at the same osmotic pressure as that of the body fluid of the intended subject, or at an increased osmotic pressure (see U.S. Pat. No. 5,094,854); the aqueous solutions may also contain some precipitated active agent, as is known in the art. A preferred active agent for encapsulation in the interior of the liposome is any water soluble, weak base agent.

The incorporation of certain active agents (such as some anesthetics) in liposomes of the present invention may additionally alter (enhance or inhibit) the release of contents from the liposome, or alter the transition temperature of the liposome, compared to that which would be seen in a similar liposome that did not contain the active agent.

The administration of antineoplastic or antitumor drugs such as doxorubicin, cisplatin and methotrexate using thermosensitive liposomes in combination with hyperthermia at the desired target site has been reported. See, e.g., Magin and Weinstein In: *Liposome Technology*, Vol. 3, (Gregoriadis, G., ed.) p. 137, CRC Press, Boca Raton, Fla. (1993); Gaber et al., *Intl. J. Radiation Oncology, Biol. Physics*, 36(5):1177 (1996).

Active agents suitable for use in the present invention include therapeutic drugs and pharmacologically active agents, nutritional molecules, cosmetic agents, diagnostic agents and contrast agents for imaging. As used herein, active agent includes pharmacologically acceptable salts of active agents. Suitable therapeutic agents include, for example, antineoplastics, antitumor agents, antibiotics, antifungals, anti-inflammatory agents, immunosuppressive agents, anti-infective agents, antivirals, anthelminthic, and antiparasitic compounds. Methods of preparing lipophilic drug derivatives which are suitable for liposome formulation are known in the art (see e.g., U.S. Pat. No. 5,534,499 to Ansell, describing covalent attachment of therapeutic agents to a fatty acid chain of a phospholipid).

In treating tumors or neoplastic growths, suitable compounds may include anthracycline antibiotics (such as doxorubicin, daunorubicin, carinomycin, Nacetyladriamycin, rubidazone, 5-imidodaunomycin, N30 acetyldaunomycin, and epirubicin) and plant alkaloids (such as vincristine, vinblastine, etoposide, ellipticine and camptothecin). Other suitable agents include paclitaxel (TAXOL®; a diterpenes isolated from the bark of the yew tree and representative of a new class of therapeutic agents having a taxane ring structure) and docetaxol (taxotere); mitotane, cisplatin, and phenesterine.

Anti-inflammatory therapeutic agents suitable for use in the present invention include steroids and non—steroidal anti-inflammatory compounds, such as prednisone, methylprednisolone, paramethazone, 11-fludrocortisol, triamciniolone, betamethasone and dexamethasone, ibuprofen, piroxicam, beclomethasone; methotrexate, azaribine, etretinate, anthralin, psoralins; salicylates such as aspirin; and immunosuppresant agents such as cyclosporine. Anti-inflammatory corticosteroids and the anti-inflammatory and immunosuppressive agent cyclosporine are both highly lipophilic and are suited for use in the present invention. Antineoplastic agents can also be used such as, for example, Navalbene.

Additional pharmacological agents suitable for use in liposomes of the present invention include anesthetics (such as methoxyflurane, isoflurane, enflurane, halothane, benzocaine, lidocane, bupivocane, and ropivicane); antiulceratives (such as cimetidine); antiseizure medications such as barbituates; azothioprine (an immunosuppressant and antirheumatic agent); and muscle relaxants (such as dantrolene and diazepam).

Imaging agents suitable for use in the present liposome preparations include ultrasound contrast agents, radiocontrast agents (such as radioisotopes or compounds containing radioisotopes, including iodo-octanes, halocarbons, and renograf in), or magnetic contrast agents (such as paramagnetic compounds).

Nutritional agents suitable for incorporation into liposomes of the present invention include flavoring compounds (e.g., citral, xylitol), amino acids, sugars, proteins, carbohydrates, vitamins and fat. Combinations of nutritional agents are also suitable.

The above active agents may be used in the various liposome embodiments described, but not limited to, those described hereinabove. Additionally, it should be emphasized that the liposomes may comprise a single pharmacologically active agent (e.g., at least one active agent) or multiple active agents, depending on the intentions of the administrator. Embodiments utilizing multiple active agents within the same liposome or in two separate liposome formulations administered together, may provide enhanced efficacy due to syngergistic behavior by the agents. By formulating and delivering multiple (e.g., two) active agents in a liposome or liposomes, and using mild hyperthermia as set forth herein, the active agents could be made to accumulate and released to a tumor at the same time or within a similar time frame.

Administration and Liposome Size

Liposomes of the present invention may be administered using methods that are known to those skilled in the art, including but not limited to delivery into the bloodstream of a subject or subcutaneous or intramuscular, or intracavity (peritneum or joint, or eye etc) administration of liposomes. Where liposomes according to the present invention are used in conjunction with hyperthermia, the liposomes may be administered by any suitable means that results in delivery of the liposomes to the treatment site. For example, liposomes may be administered intravenously and thereby brought to the site of a tumor by the normal blood flow; heating of this site can result in greater liposome extravasation from the blood stream because of the effect of hyperthermnia on blood vasculature and moreover, once extravasated into the tumor tissue results in the liposomal membranes being heated to the phase transition temperature so that the liposomal contents are preferentially released at the site of the tumor.

Where treatment of a tumor or neoplasm is desired, effective delivery of a liposome-encapsulated active agent via the bloodstream requires that the liposome be able to penetrate the continuous (but "leaky") endothelial layer and underlying basement membrane surrounding the vessels supplying blood to a tumor. Liposomes of smaller sizes have been found to be more effective at extravasation into tumors through the endothelial cell barrier and underlying basement membrane which separates a capillary from tumor cells. See, e.g., U.S. Pat. No. 5,213,804 to Martin et al.

As used herein, "solid tumors" are those growing in an anatomical site other than the bloodstream (in contrast to blood-borne tumors such as leukemias). Solid tumors require the formation of small blood vessels and capillaries to nourish the growing tumor tissue.

In accordance with the present invention, the anti-tumor or anti-neoplastic agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration, but also by, for example, direct injection. Tumors characterized by an acute increase in permeability of the vasculature in the region of tumor growth are particularly suited for treatment by the present methods. Administration of liposomes is followed by heating of the treatment site to a temperature that results in release of the liposomal contents.

Where site-specific treatment of inflammation is desired, effective liposome delivery of an active agent requires that the liposome have a long blood halflife, and be capable of penetrating the continuous endothelial cell layer and underlying basement membrane surrounding blood vessels adjacent to the site of inflammation. Liposomes of smaller sizes have been found to be more effective at extravasation through the endothelial cell barrier and into associated inflamed regions. See, e.g., U.S. Pat. No. 5,356,633 to Woodle et al. In accordance with the present invention, the anti-inflammatory agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Inflamed regions characterized by an acute increase in permeability of the vasculature in the region of inflammation, and by a localized increase in temperature, are particularly suited for treatment by the present methods.

It will further be appreciated that the liposomes of the present invention may be utilized to deliver anti-infective agents to sites of infection, via the bloodstream. The use of liposomes containing a vesicle-forming lipid derivatized with a hydrophilic polymer, and having sizes ranging between 0.07 and 0.2 microns, to deliver therapeutic agents to sites of infection is described in published PCT patent application WO 93/19738. In accordance with the present invention, the anti-infective agent of choice is entrapped within a liposome having a membrane according to the present invention, and the resulting liposomal formulation is administered parenterally to a subject, preferably by intravenous administration. If desired, localized hyperthermia may be induced at the site of infection to cause the preferential release of liposomal contents at that site.

The size of liposomes in a preparation may depend upon the active agent contained therein and/or the intended target. Liposomes of between 0.05 to 0.3 microns in diameter, have been reported as suitable for tumor administration (U.S. Pat. No. 5,527,528 to Allen et al.). Sizing of liposomes according to the present invention may be carried out according to methods known in the art, and taking into account the active agent contained therein and the effects desired (see, e.g., U.S. Pat. No. 5,225,212 to Martin et al; U.S. Pat. No. 5,527,528 to Allen et al., the disclosures of which are incorporated herein by reference in their entirety). A preferred embodiment of the present invention is a liposome of less than 10 microns in diameter, or a liposome preparation containing a plurality liposomes of less than 10 microns in diameter. In a further preferred embodiment of the present invention, liposomes are from about 0.05 microns or about 0.1 microns in diameter, to about 0.3 microns or about 0.4 microns in diameter. Liposome preparations may contain liposomes of different sizes. Advantageously, these liposomes comprise lipid mixtures set forth herein and are therefore temperature-sensitive, with an ability to release contained drug, as described.

In another preferred embodiment of the present invention, liposomes are from about 50 nm, 100 nm, 120 nm, 130 nm, 140 nm or 150 nm, up to about 175 nm, 180 nm, 200 nm, 250 nm, 300 nm, 350 nm, 400 nm or 500 nm in diameter.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

In a further aspect of the present invention, liposomes are dispersed in physiological saline or PBS to provide an aqueous preparation of liposomes. The aqueous preparation may further include an equilibrating amount of the surface active agent contained in the liposome bilayer, to reduce or prevent loss of the surface active agent from the liposome bilayer into solution. Liposomes composed of DPPC:MPPC may be contained in physiological saline or PBS that contains from about 1 microMolar to about 5 microMolar of MPPC monomer.

The amount of active agent to be entrapped within or carried by liposomes according to the present invention will vary depending on the therapeutic dose and the unit dose of the active agent, as will be apparent to one skilled in the art. In general, however, the preparation of liposomes of the present invention is designed so the largest amount of active agent possible is carried by the liposome. Liposomes of the present invention may be of any type, however, LUVs are particularly preferred.

The liposomes of the invention can be used in other applications such as, for example, an anesthetic release. Moreover, in addition to the above, the liposomes may be used to treat various non-malignant diseases such as, but not limited to, psoriasis and arthritis. The administration of the liposomes in these applications may be carried out according, but not limited to, techniques described herein. In various embodiments, especially for anticancer therapies or where drugs act at particular points in the cell cycle, the liposomes may be delivered in multiple short pulses over extended time periods, such as by employing pulse heat. Examples of active agents that could be delivered in this manner include, but are not limited to, cell cycle dependent drugs such as, for example, camptothecins and vinca alkaloids. In other embodiments, active agents may be delivered in a single protracted release including, for example, anthracyclines (e.g., doxorubicin). The selection of active agents for use in the various techniques may be made by the skilled artisan.

Assessing Release of Liposome Contents

Characterization of thermosensitive liposomes by the release of an entrapped fluorescent probe, 6-Carboxyfluorescein (CF), was reported in Merlin, *Eur. J. Cancer* 27(8): 1031 (1979). CF was entrapped into liposomes at a quenching concentration (50 mM); no fluorescence was observed for CF entrapped in the liposome.

Intense fluorescence, however, developed upon release of the probe from liposomes due to dilution of the CF in the suspension. The amount of the probe released from the liposomes at various temperatures could thus be quantified based on fluorescence. Merlin, *Eur. J. Cancer.*, 27(8):1031 (1991), studied thermally sensitive liposomes encapsulating Doxorubicin (DX), and incorporated pegylated lipids in the bilayer to increase their circulation time in the blood stream compared to conventional thermosensitive liposomes. See also Maruyama et al., *Biochem. Biophys. Acta*, 1149:17 (1993)).

The examples which follow are set forth to illustrate the present invention, and are not to be construed as limiting thereof.

EXAMPLE 1

Preparation of Temperature—Sensitive Liposomes

DPPC liposomes containing varied molar concentrations of the lysolipid Monopalmitoylphosphatidylcholine (MPPC) were prepared and characterized. The aqueous fluorescent probe 6-Carboxyfluorescein (CF) was entrapped within the liposomes to act as a marker for membrane permeability change; CF was incorporated into the liposomes using methods known in the art (See, e.g., *Liposomes: A Practical Approach* (1990), Editor: R. R. C. New, IRL Press, Oxford, N.Y.). The liposome components were dissolved in chloroform (a suitable organic solvent), and the solvent was evaporated under vacuum at 45° C. using a rotavapor to form a uniform thin film of lipids on the inner walls of a round bottom flask. The lipid film was further dried under vacuum for 25 hours to ensure complete removal of traces of chloroform.

The lipid film was hydrated at 45° C. with an aqueous solution of 10 mM PBS (pH=7.4) containing 50 mM CF and 1 microM MPPC. For efficient hydration, a TEFLON® bead was used to gently etch the lipids in the presence of aqueous medium to form a cloudy suspension of multilamellar vesicles (MLVs). The MLVs thus formed had an average size of 700 nm and were extruded through a stack of two polycarbonate membrane filters of 0.1 micrometers under 300–400 psi pressure at 45° C. (i.e., above the gel-liquid crystalline temperature of the lipid or lipid mixture) as described in the method developed by Hope et al. (*Biochem. Biophys. Acta* 812:55–65 (1985)) to obtain Large Unilamellar Vesicles by Extrusion Technique (LUVETs) of the desired 140 nm size. The mean diameter of the vesicles was measured by Photon Correlation Spectrometer (PCS, Coulter, N4 plus) after each extrusion pass.

Figure 2:
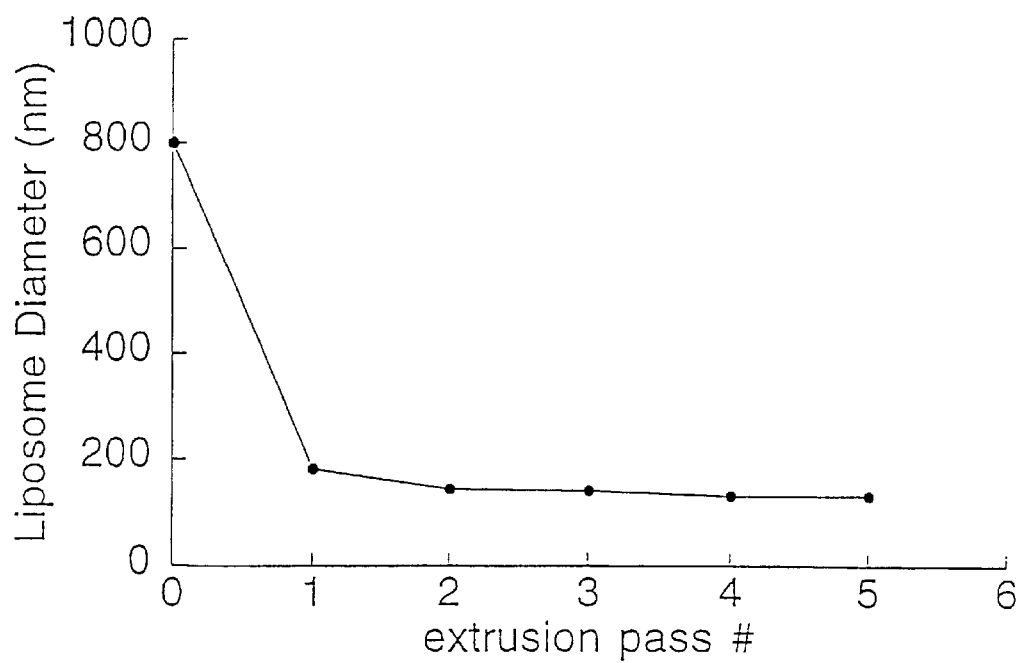
FIG. 2 graphs the effect of extrusion pass on the mean diameter of DPPC liposomes containing DPPC:MPPC (90:10). Multilamellar vesicles with an average size of 700 nm were extruded through a stack of two polycarbonate membranes of pore size 0.1 mM under a pressure of 300–400 psi at 45° C.

As shown in FIG. 2, the size of liposomes decreased with successive passes through the membrane and reached the minimum size after three passes.

EXAMPLE 2

Release of Liposomal Contents

The in vitro stability and thermosensitivity of the liposomal formulations prepared as described in Example 1 and containing various molar fractions of MPPC was assessed by measuring the percent release of entrapped water soluble fluorescent molecule, CF, from the aqueous interior of the vesicle to the surrounding solution as a function of incubation temperature (25–45° C.) in the presence of PBS. The fluorescence of CF entrapped in the liposomes was self quenched due to its high concentration, but upon release from the liposomes and dilution into the suspending medium, CF developed an intense fluorescence. After incubation, the fluorescence intensity of the samples was measured at excitation wavelength ($\lambda$ex)=470 nm and emission wavelength ($\lambda$em)=520 nm after suitable dilutions to determine the amount of CF released from the liposomes. The relative percent fluorescence intensity due to incubation at a particular temperature was calculated by comparison with the total release of entrapped material obtained after disruption of the liposome samples by adding 10% Triton X-100.

This experiment was carried out for liposomes composed of pure DPPC and for liposomes composed of DPPC:MPPC mixtures containing 2, 4, 6, 7, 8, 10 or 20 mol % MPPC, over the temperature range 20° C. to 45° C.

Figure 3:
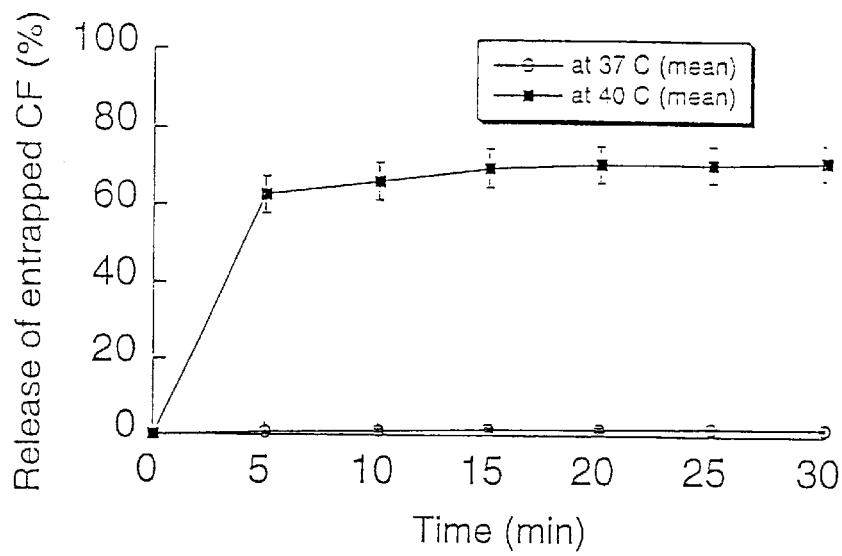
FIG. 3 graphs the release of 6-Carboxyfluorescein (CF) entrapped in liposomes composed of DPPC:MPPC (90:10), as a function of time in the presence of PBS at 37° (open circles) and 40° C. (closed squares).

The amount of entrapped CF released from liposomes of the present invention was measured as a function of time at physiological (37° C.) and hyperthermic (40° C.) temperatures. Liposomes were incubated in PBS for various time intervals and the release of CF was measured fluorimetrically at $\lambda$ex=470 nm and $\lambda$em=520 nm. Typical heating runs are shown in FIG. 3, for the 90:10 DPPC:MPPC composition. At 37° C. the percent release of CF was negligible. However, on incubation at 40° C., about 60% of the entrapped CF was released within five minutes; additional contents release only increased slightly upon further incubation at this temperature. Thus at a given temperature, most of the contents are released within the first five to ten minutes of heating.

Figure 4:
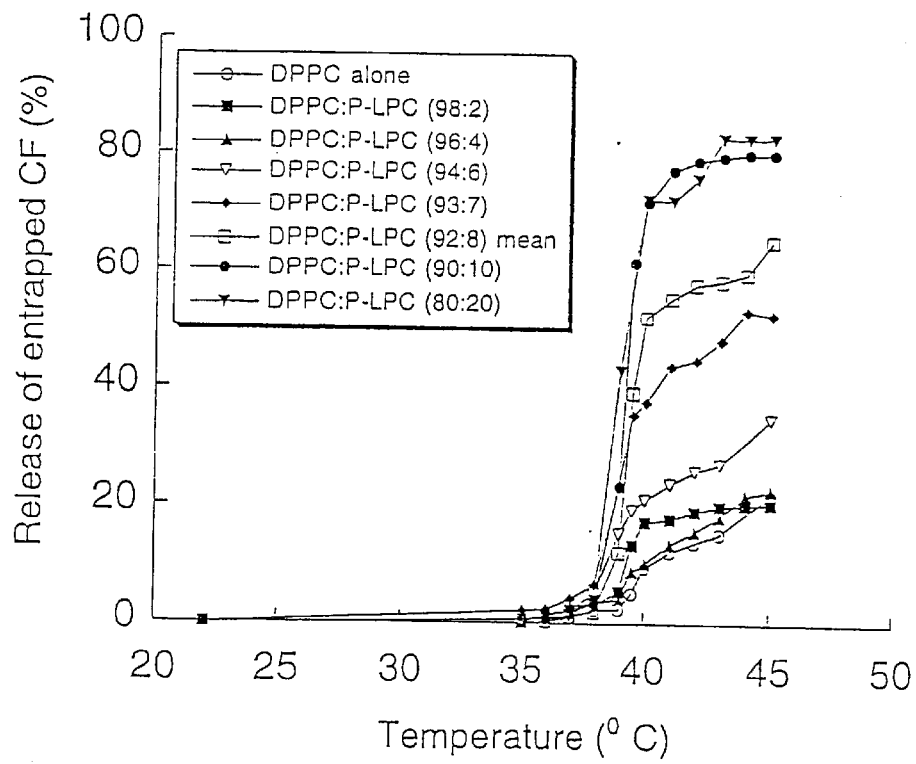
FIG. 4 graphs the release of CF from DPPC:MPPC liposomes of varied concentrations, at temperatures between 20° C. and 45° C. in the presence of 10 mM PBS (pH=7.4). Liposomes contained DPPC alone (open circles); DPPC:MPPC 98:2 (closed squares); DPPC:MPPC 96:4 (closed triangles ▼); DPPC:MPPC 94:6 (open triangles ▽); DPPC:MPPC 93:7 (closed diamonds); DPPC:MPPC 92:8 (open squares); DPPC:MPPC 90:10 (closed circles); DPPC:MPPC 80:20 (closed triangles ▲).

FIG. 4 shows the release of CF from liposomes incubated for five minutes at temperatures of 20° C. to 45° C. in the presence of 10 mM PBS (pH=7.4). Release of CF was measured fluorimetrically at $\lambda$ex=470 nm and $\lambda$em=520 nm. The percent of CF released was calculated by comparing the values obtained with those obtained after the total release of CF (achieved by the addition of Triton X-100 to the liposome sample to dissolve the liposomes and release all entrapped CF). Pure DPPC liposomes were stable up to 39.5° C. but became permeable near the transition temperature of the phospholipid, thus causing release of some of the CF. The amount of CF released from the pure DPPC liposome was, however, only about 20% of total contents. In contrast, with increasing concentrations of MPPC in the DPPC bilayers, liposomes showed an increasing release of CF, with maximum release occurring for the liposomes having bilayers containing 10 mol % and 20 mol % MPPC.

These results demonstrate that the incorporation of as little as 10 mol % of MPPC into the membranes of DPPC liposomes increases the amount of CF released by a factor of 4 (compared to the release that is seen for liposomes of DPPC alone), allowing release of up to 90% of the liposomal contents.

The temperature release profiles also show an additional benefit of incorporating MPPC into DPPC liposome membranes, in that the onset temperature for release is shifted to slightly lower temperatures, starting at approximately 38° C. for liposomes containing 10 mol % and 20 mol % MPPC. The release profile is sharp for these liposomes, and the maximum amount of CF is released after a rise in temperature of only a degree or so, i.e., at between 38.5° C. and 40° C. for the 10% MPPC liposomes.

These experiments demonstrate that the inclusion of MPPC in liposome bilayers made of DPPC increases the amount of contents released from the interior of the liposome, and shifts the temperature range over which release occurs into the range of 38.5° C.–40° C., which is the mild hyperthermic range.

In DPPC liposomes containing MPPC concentrations of more than 20 mol %, the liposomes became intrinsically unstable and therefore unable to retain entrapped material at temperatures above the lipid phase transition (i.e., in the liquid phase of the lipid bilayer that occurs during processing of liposomes). Such high concentrations of MPPC can also destabilize the gel phase bilayers at temperatures below the transition temperature. As demonstrated previously, the mechanical strength of membranes decreases as more and more MPPC is included (Needham et al., *Biophys. J.* 73:2615 (997)), and the bilayers eventually make a transition to a pure micelle suspension as the mole ratio of MPPC to phospholipid goes beyond 50 mol % (Zhelev et al., *Biophys. J.* (in press; 1998)). One preferred molar ratio for thermally sensitive liposomes is 90:10, DPPC:MPPC.

EXAMPLE 3

Figure 5B:
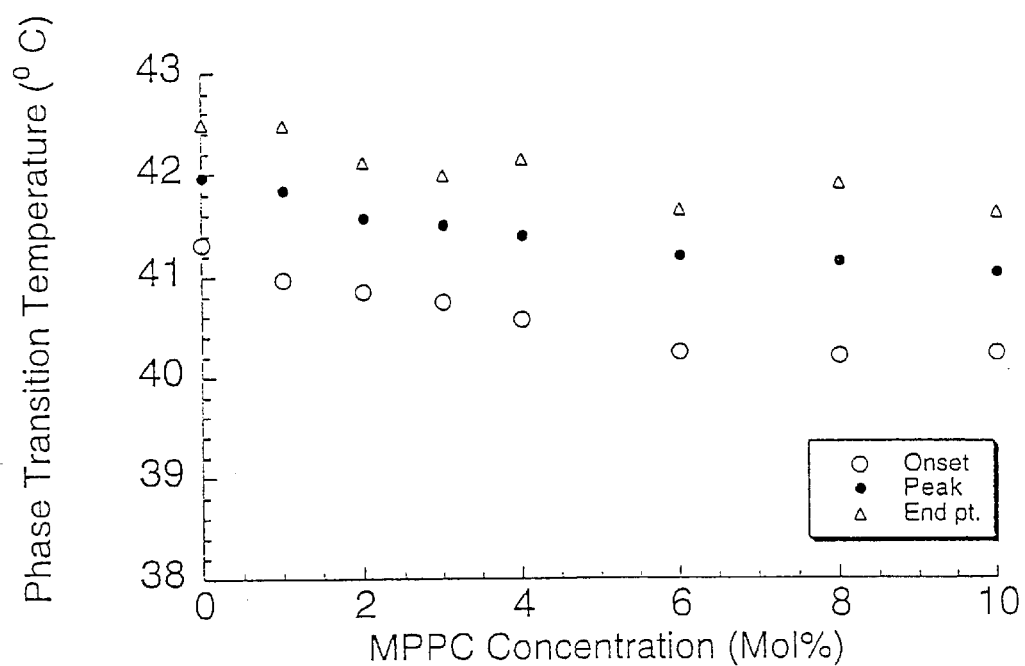
FIG. 5B graphs the effect of MPPC concentration on the phase transition temperature (Tc) of DPPC liposomes, as described above for FIG. 5A. The graph shows the start point of the transition (open circle); the peak in enthalpy (closed circle); and the end point of the transition (open triangle).
Figure 5A:
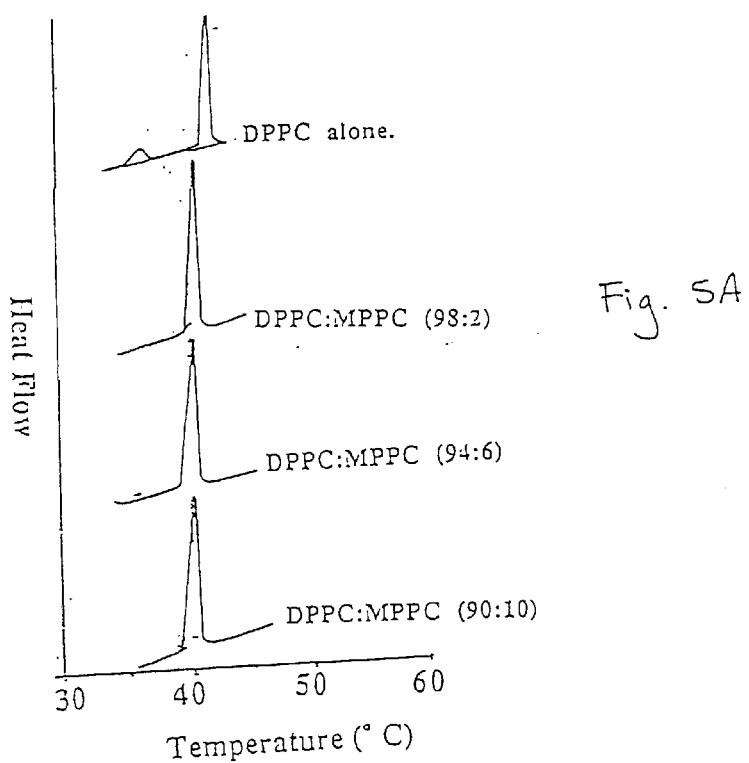
FIG. 5A provides heat flow thermograms showing the effect of varied MPPC concentration on the phase transition temperature (Tc) of DPPC liposomes. The Tc of lyophilized liposomal samples of DPPC containing MPPC (1–10 mol %) was measured by Differential Scanning Calorimetry (DSC) between 30° C.–45° C. with 2 C°/minute heating rate.

Phase Transition Behavior of DPPC/MPPC Mixtures and Correlations With Release Temperatures To investigate the biophysical mechanism involved in the permeability of the liposomes of the present invention, differential scanning calorimetric (DSC) studies were carried out to generate differential calorimetric thermograms for the present liposomes, to determine the phase transition temperature. These results were compared with the release versus temperature scans obtained from cumulative release profiles (shown in FIG. 4). FIGS. 5A and 5B show the heat flow thermograms for liposome preparations containing increasing concentrations of MPPC in DPPC bilayers. These thermograms show that the transition temperature remains unbroadened even though up to 10% of MPPC are included in the bilayer. At a higher level of resolution, FIG. 5B shows the change in the peak of the transition temperature from 41.9° C. to 41.04° C. as the MPPC composition is increased from zero to 10 mol % in DPPC bilayers. Also shown is the breadth of the transition, represented as the start and end point of the transition, i.e., the solidus and liquidus lines below and above the excess heat flow peak.

Figure 6A:
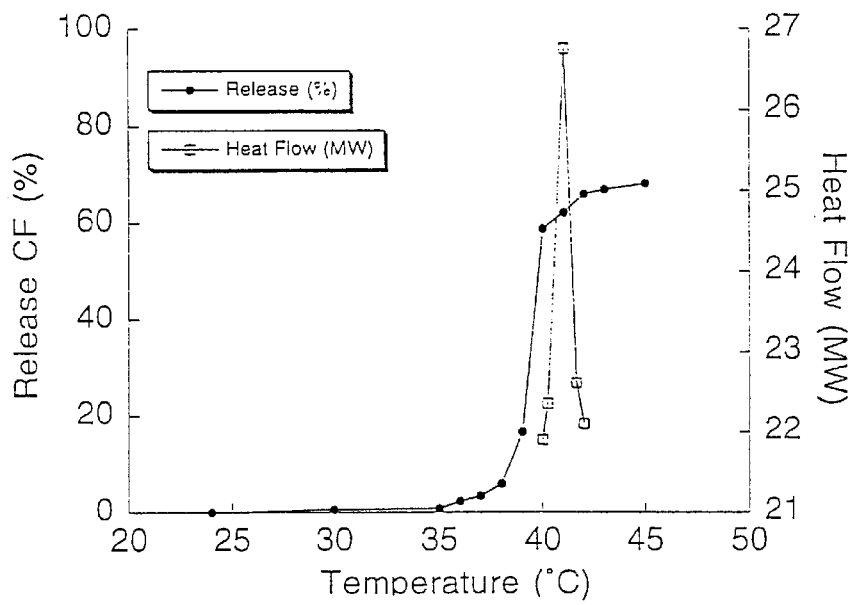
FIG. 6A compares the differential scanning calorimetric profile (excess heat flow; open squares) of liposomes (90:10 DPPC:MPPC) with the differential release profile (solid circles) for 6-Carboxyfluorescein (CF) release, as obtained from the cumulative release experiment described in FIG. 4.

The differential scanning thermogram of liposomes of the present invention can be compared with the differential release profiles. FIG. 6A shows the cumulative release profile for CF release from the DPPC:MPPC 90:10 liposomes versus temperature, and the heat flow thermogram over the same temperature range.

Figure 6B:
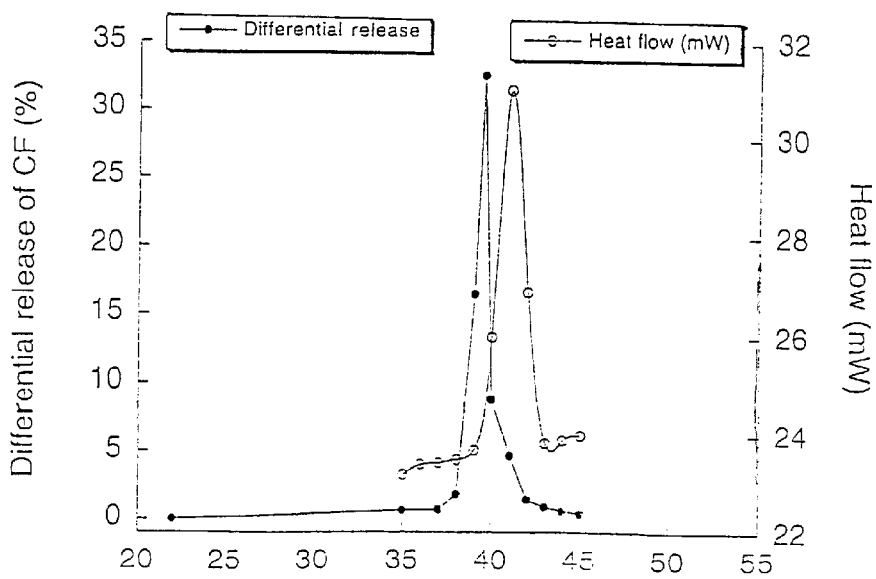
FIG. 6B graphs the differential release profile from 90:10 DPPC:MPPC liposomes, where open circles represent heat flow and solid circles represent differential release of CF over temperatures of from 25° C. to 45° C.

FIG. 6B shows the differential release, which highlights the sharpness of the release profile and the temperature at which maximum release occurs in relation to the heat flow thermogram. What is striking about this comparison is that that the peak release of contents obtained from the differential release profiles was 0.9° C. lower than the peak in the transition enthalpy obtained by DSC. The release of the entrapped material at the temperature prior to Tc can be attributed to the fact that the release is occurring at the 'solidus' line of the thermogram and not at the peak temperature. One explanation for such a behavior is that the release of entrapped material occurs as soon as the 'first defects' (melting defects) in the microdomain boundaries of the bilayer network appear; it is here that the lysolipid may exert its effects. While not wishing to be held to a single theory, the present inventors suspect that as the transition temperature is approached the first parts of the microstructure that melt are at the grain boundaries of the solid membrane. When surrounded by a lysolipid-free aqueous phase, the lysolipid is trapped in the gel phase but can desorb when the membrane begins to melt; as it does so it enhances the defect permeability and the contents are released more effectively than in liposomes of pure lipid alone.

EXAMPLE 4

Entrapment and Release of Doxorubicin

Doxorubicin (DX) was entrapped into the inner aqueous volumes of liposomes of the present invention (DPPC:MPPC 90:10) using the pH gradient-driven encapsulation protocol (L. D. Mayer et al (1989) *Cancer Res.*, 42:4734.).

Briefly, a lipid composition of 90:10 DPPC:MPPC was dissolved in chloroform and the solvent was evaporated under vacuum at 45° C. using a rotavapor. The lipid film obtained after further drying in the vacuum desiccator overnight was hydrated with 300 mM citrate buffer (pH 4.00) and the multilamellar vesicles formed were subjected to seven freeze-and-thaw cycles. The resulting suspension was extruded through two polycarbonate membrane filters of pore size 0.1 $\mu$M at 50° C. using 300–400 psi pressure. The extruded liposomes were allowed to cool to room temperature and the pH was raised to 7.5–8.0 using 0.5 M $Na_2CO_3$ solution.

The extruded liposomes were incubated at 60° C. for five minutes before adding pre-heated DX to the suspension. Samples were further heated for 10 minutes at 60° C. with intermittent vortexing. The unentrapped drug was removed by mini-column centrifugation using Sephadex G-50 gel.

Figure 7:
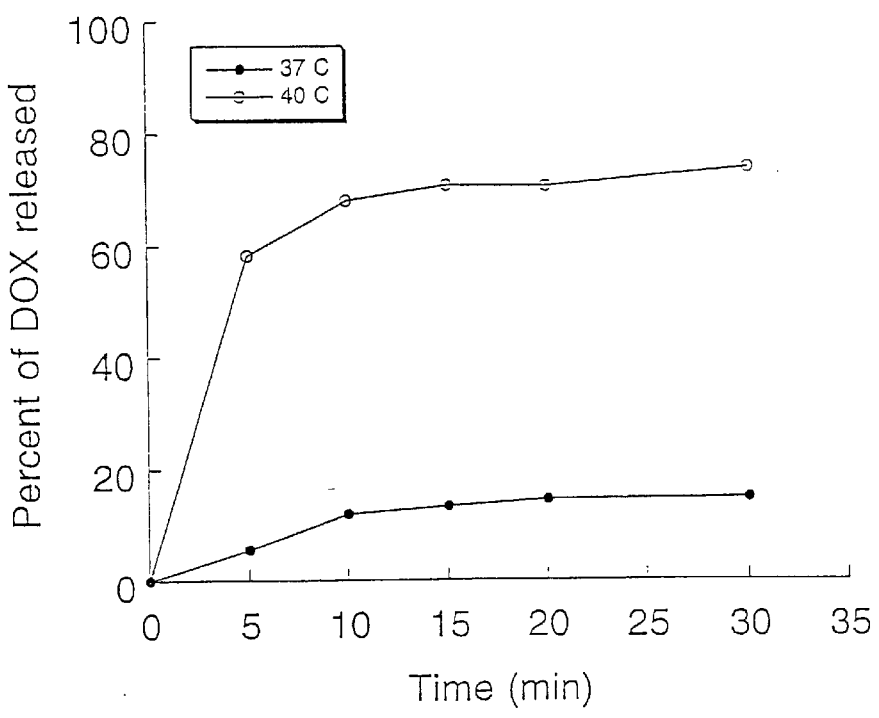
FIG. 7 graphs the release of entrapped Doxorubicin (DX) from liposomes (90:10 DPPC:MPPC) as a function of time at 37° C. (solid circles) and 40° C. (open circles) in the presence of PBS.

The DX entrapped liposomes were characterized by the release of DX from liposomes in the presence of PBS as a function of time at 37° and 40° C., as well as by the cumulative release profiles of entrapped DX from the liposomes at various temperatures between 25°–45° C. FIG. 7 represents the release of entrapped DX from liposomes as a function of time at 37° C. and 40° C. the liposomes were incubated at 37° and 40° C. for 30 minutes and the fluorescence intensity of the released DX was measured after suitable dilutions at $\lambda ex=470$ nm and $\lambda em=585$ nm. The percent release was calculated by comparing these values with values for the total release of 6-Carboxyfluorescein (obtained by the addition of Triton X-100 to the liposome sample). As can be seen from FIG. 7, about 14% of the DX was released at 37° C. after 30 minutes of incubation, whereas 73% of the drug was released at 40° C. after 30 minutes.

Figure 8:
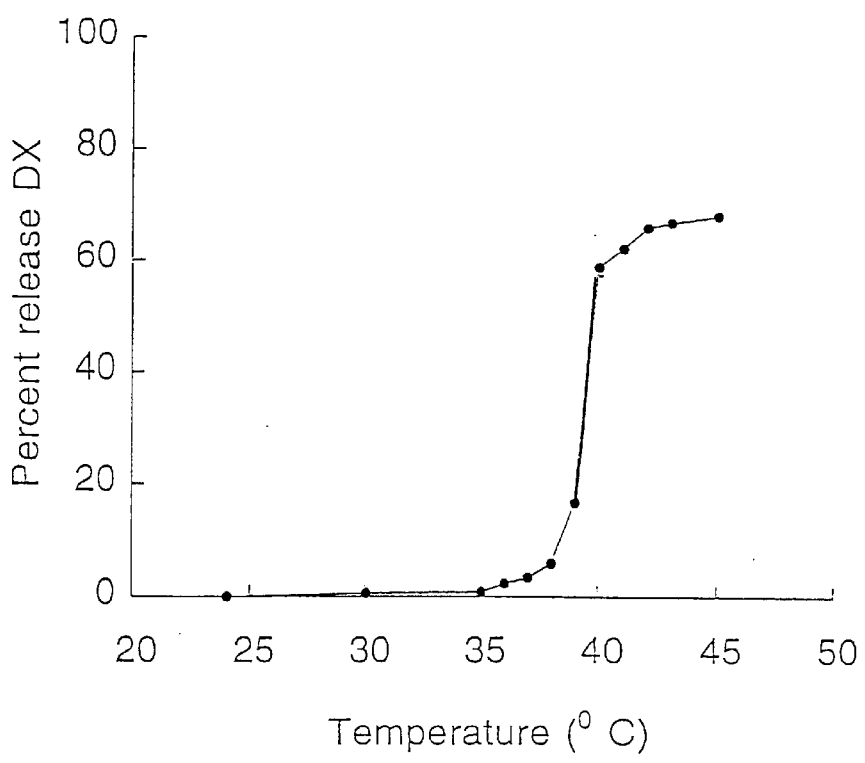
FIG. 8 graphs the cumulative release profiles of entrapped DX from liposomes composed of 90:10 DPPC:MPPC, incubated at temperatures of between 25° C. and 45° C. for five minutes in the presence of PBS.

As with the above studies (Examples 1–3) using CF, the cumulative release of DX entrapped in DPPC:MPPC 90:10liposomes was measured by incubating the samples at various temperatures between 25°–45° C. for five minutes and measuring the released DX fluorimetrically, as shown in FIG. 8. The results showed about 23% release of DX up to 39° C. and reached 65% release at 40° C.

EXAMPLE 5

Inclusion of PEG in Liposome Bilayers

Liposomes of the present invention were modified to render them less recognizable by the RES, thereby enhancing their half life in the blood circulation.

Figure 11C:
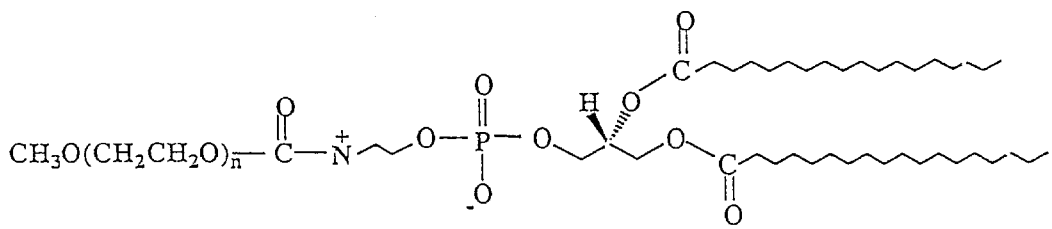
FIG. 11C shows the chemical structure of 1,2-Distearoyl-sn-Glycero-3-Phosphoethanolamine-N-[Poly(ethyleneglycol) 2000] (DSPE-PEG2000).

The surface of liposomes containing DPPC:MPPC 90:10 was modified by incorporating 5 mol % of DSPE-PEG (M.W. 2000) (FIG. 11C) in the liposome composition. Thus, the modified composition of these liposomes was DPPC:MPPC:DSPE-PEG-2000 (85.935:9.545:4.520).

EXAMPLE 6

Influence of Biological Fluids on Release of Liposome Contents

Surface-modified liposomes as described in Example 5 were characterized by studying the release profiles of CF entrapped in the aqueous interior liposomal region in the presence of either PBS or 50% bovine serum. The fluorescent intensity of released CF was measured at $\lambda ex=470$ nm and $\lambda em=520$ nm, and the percent release was calculated as described in Example 3.

Figure 9A:
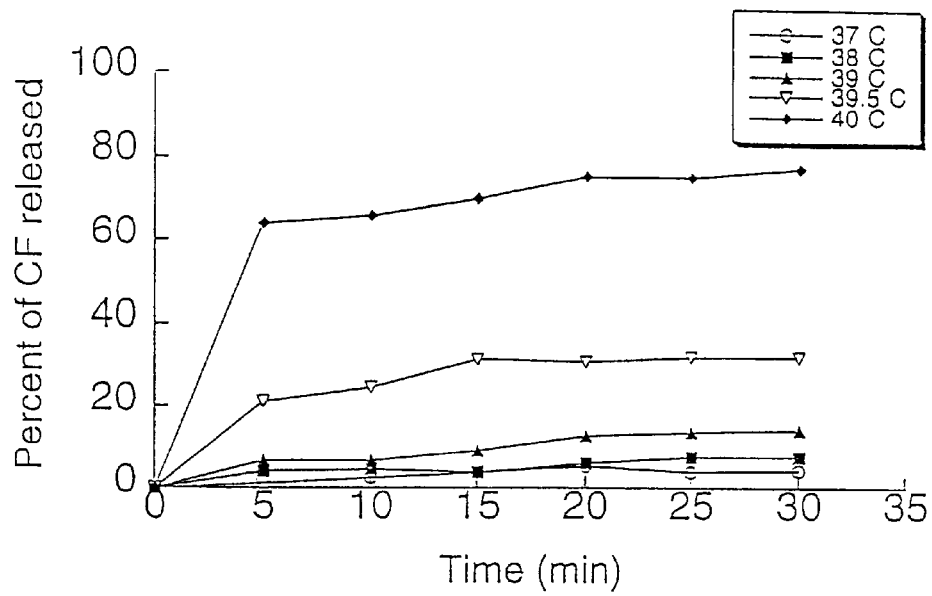
FIG. 9A graphs the release of entrapped 6-Carboxyfluorescein (CF) from liposomes (90:10 DPPC:MPPC incorporated with 5 mol % of DSPE-PEG2000) in the presence of PBS and as a function of temperature (37° C.—open circle; 38° C.—closed square; 39° C.—closed triangle; 39.5° C.—open triangle; and 40° C.—closed circle).
Figure 9B:
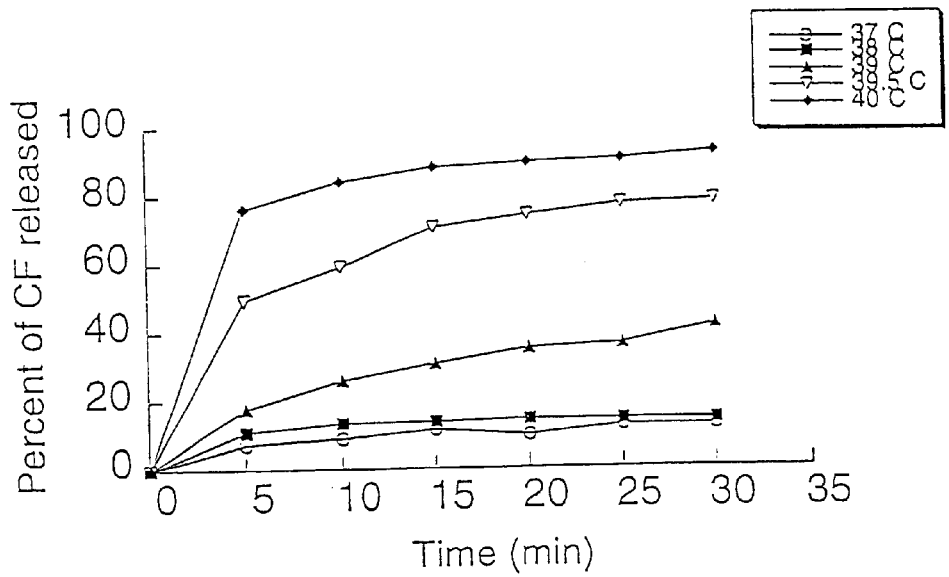
FIG. 9B graphs the release of entrapped 6-Carboxyfluorescein (CF) from liposomes (composed of 90:10 DPPC:MPPC and incorporated with 5 mol % of DSPE-PEG2000) in the presence of 50% bovine serum and as a function of temperature (37° C.—open circle; 38° C.—closed square; 39° C.—closed triangle; 39.5° C.—open triangle; and 40° C.—closed circle).
Figure 10:
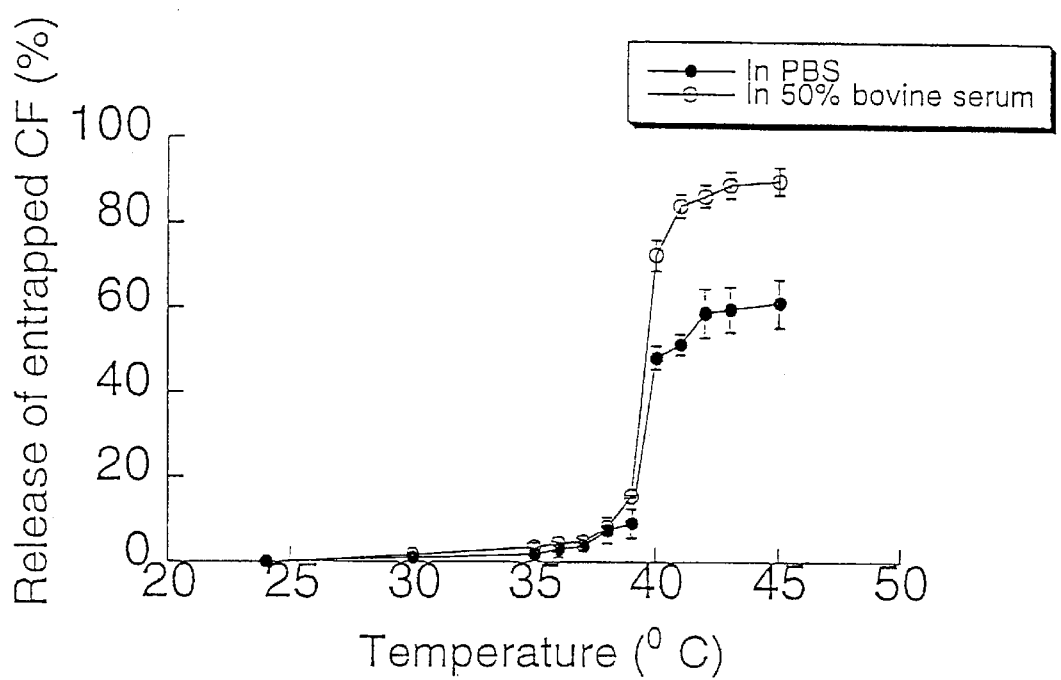
FIG. 10 graphs the cumulative release of entrapped 6-Carboxyfluorescein (CF) from liposomes composed of 90:10 DPPC:MPPC, at various temperatures from 25° to 45° C. in the presence of PBS (closed circles) or 50% bovine serum (open circles).

FIG. 9A shows the release of entrapped CF at 37° to 40° C. as a function of time, in the presence of PBS. FIG. 9B shows the release of entrapped CF at 37° to 40° C. as a function of time, in the presence of 50% bovine serum. The surface modified liposome formulation of the present invention was stable at physiological temperature (37° C.) in the presence of PBS and serum, showing 1% and 7% of CF release, respectively. However, incubation of these liposomes at 40° C. showed 64% (in PBS) and 76% (in serum) release of entrapped CF after five minutes of incubation, and reached 77% (in PBS) and 92% (in serum) after 30 minutes' incubation. Cumulative release profiles of entrapped CF from liposomes in the presence of PBS and 50% bovine serum showed 58% and 73% release, respectively (FIG. 10). While not wishing to be held to a single theory, the enhanced release of CF in the presence of serum could be attributable to the interaction of certain small molecule blood components in the serum with the liposome surface.

EXAMPLE 7

Effect of Lysolipid Concentration on Transition Enthalpy of Lipid Bilyer

Figure 13:
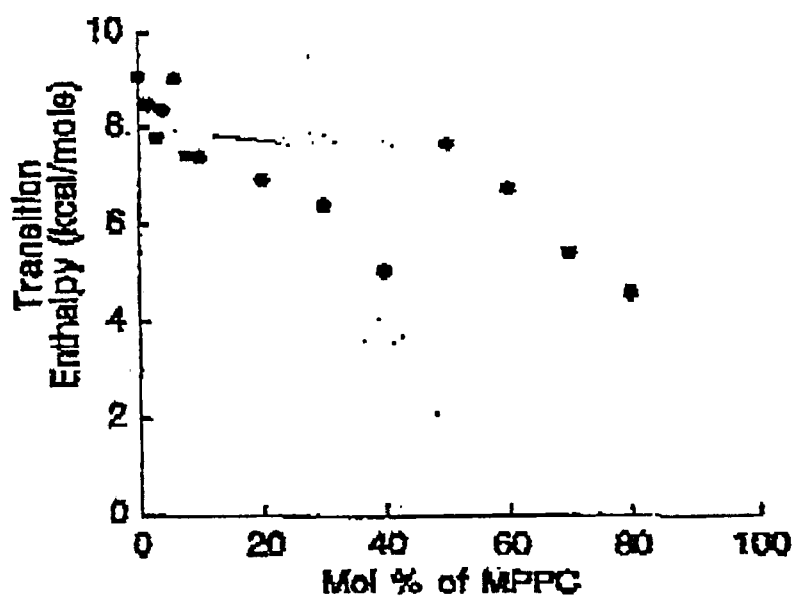
FIG. 13 shows the transition enthalpy for lipid bilayers having various concentrations of DPPC and MPPC.

Various liposomes were prepared according to the methods set forth herein employing DPPC as phospholipid and MPPC as surface active agent, i.e., lysolipid. The transition enthalpy for bilayers with varying concentrations of DPPC and MPPC were determined as set forth in FIG. 13. As shown, the enthalpy initially decreased but then increased abruptly to a maximum at a 50:50 DPPC/MPPC molar ratio. Thus, this concentration level produces stable gel phase bilayer and the large amount of lysolipid allows for a heightened release of active agent that is present within the liposome. The large amounts of lysolipid released may also have a local therapeutic effect and therefore enhance the efficacy of drug containing liposomes

EXAMPLE 8

Effect of Loading Doxorubicin in a Liposome Below its Phase Transition Temperature Doxorubicin was loaded into a lysolipid-containing temperature sensitive liposome at 37° C., i.e., a temperature below its transition temperature. As a result, 80 percent of the doxorubicin loaded into the liposome, which was an improvement over the 30 to 40 percent loading that occurs using conventional loading techniques, namely a temperature of 60° C., which is above the phase transition of the lipid mixture.

The foregoing examples are illustrative of the present invention, and are not to be construed as limiting thereof. The invention is described by the following claims, with equivalents of the claims to be included therein.

What is claimed is:

1. A liposome, comprising a gel-phase lipid bilayer membrane having a phase transition temperature, and an active agent, wherein the gel-phase lipid bilayer membrane comprises:
(a) one or more phospholipids selected from the group consisting of phosphatidyl cholines, phosphatidyl glycerols, phosphatidyl inositols, and phosphatidyl ethanolamines, wherein the one or more phospholipids have two acyl groups; and
(b) one or more lysolipids selected from the group consisting of monoacylphosphatidyl cholines, monoacylphosphatidylglycerols, monoacylphosphatidylinositols, and monoacylphosphatidylethanolamines, wherein the one or more lysolipids have one acyl group; and wherein the active agent is selected from the group consisting of a pharmacologically active agent or a diagnostic agent; and wherein the phase transition temperature is 39 to 45° C., and, wherein the amount of the one or more lysolipids in the gel-phase lipid bilayer membrane is sufficient to increase a first percentage of active agent released from the liposome at the phase transition temperature, compared to a second percentage of active agent released in the absence of the one or more lysolipids.

2. The liposome of claim 1, wherein the phospholipid and lysolipid are contained in a molar ratio of from 99:1 to 51:49.

3. The liposome of claim 1, wherein the phospholipid and lysolipid are contained in a molar ratio of from 99:1 to 70:30.

4. The liposome of claim 1, wherein the acyl groups of the phospholipids are saturated.

5. The liposome of claim 1, wherein the lysolipid is monopalmitoylphosphatidylcholine (MPPC), monolaurylphosphatidylcholine (MLPC), monomyristoylphosphatidylcholine (MMPC), monostearoylphosphatidylcholine (MSPC), and mixtures thereof.

6. The liposome of claim 5, wherein the lysolipid is monostearoylphosphatidylcholine (MSPC).

7. The liposome of claim 6, wherein the lysolipid is monostearoylphosphatidylcholine (MSPC) and the phospholipid is dipalmitoylphosphatidylcholine (DPPC).

8. The liposome of claim 5, wherein the lysolipid is monopalmitoylphosphatidylcholine (MPPC) and the phospholipid is dipalmitoylphosphatidylcholine (DPPC).

9. The liposome of claim 1, wherein the active agent is entrapped within the interior of the liposome.

10. The liposome of claim 1, wherein the active agent is entrapped within the gel-phase lipid bilayer membrane.

11. The liposome of claim 1, having a diameter of from about 50 nanometers to about 400 nanometers.

12. The liposome of claim 1, wherein the gel-phase livid bilayer membrane further comprises a phospholipid derivatized with a hydrophilic polymer.

13. The liposome of claim 12, wherein the hydrophilic polymer is selected from the group consisting of polyethylene glycol, polylactic acid, polyglycolic acid, copolymers of polylactic acid and polyglycolic acid, polyvinyl alcohols, polyvinylpyrrolidone, oligosaccharides, and mixtures thereof.

14. The liposome of claim 1, wherein the active agent is a pharmacologically active agent selected from the group consisting of anesthetics, antihistamines, antineoplastics anti-ulceratives, anti-seizure agents, muscle relaxants, immunosuppressive agents, anti-infective agents, non-steroidal anti-inflammatory agents, imaging agents, nutritional agents, and mixtures thereof.

15. The liposome of claim 14, wherein the active agent is selected from the group consisting of antineoplastic agents, non-steroidal anti-inflammatory agents, immunosuppressive agents, and anti-infective agents.

16. The liposome of claim 14, wherein the active agent is an antihistamine.

17. The liposome of claim 14, wherein the active agent is an antineoplastic agent or antitumor agent.

18. The liposome of claim 14, wherein the active agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methyl-prednisone, and navalbene.

19. The liposome of claim 18, wherein the active agent is paclitaxel.

20. The liposome of claim 18, wherein the active agent is camptothecin.

21. The liposome of claim 18, wherein the active agent is doxorubicin.

22. The liposome of claim 14, wherein the active agent is a non-steroidal anti-inflammatory agent.

23. The liposome of claim 22, wherein the active agent is ibuprofen.

24. A method of administering an active agent to a preselected target site in a subject's body, comprising:
(a) administering a liposome containing the active agent, wherein the liposome comprises a gel-phase lipid bilayer membrane having a phase transition temperature, and an active agent,
wherein the gel-phase lipid bilayer membrane comprises:
(i) one or more phospholipids selected from the group consisting of phosphatidyl cholines, phosphatidyl glycerols, phosphatidyl inositols, and phosphatidyl ethanolamines, wherein the phospholipids have two acyl groups; and
(ii) one or more lysolipids selected from the group consisting of monoacylphosphatidylcholines, monoacylphosphatidylglycerols, monoacylphosphatidylinositols, and monoacylphosphatidylethanolamines, wherein the one or more lysolipids have one acyl group; and
wherein the active agent is selected from the group consisting of a pharmacologically active agent or a diagnostic agent; and
(b) heating the subject's preselected target site to a temperature about 39° C. to 45° C. to release the active agent from the liposome at the target site;
wherein the amount of the one or more lysolipids in the lipid bilayer membrane is sufficient to increase a first percentage of active agent released from the liposome at the phase transition temperature, compared to a second percentage of active agent released in the absence of the one or more lysolipids.

25. The method of claim 24, wherein the preselected target site comprises a solid tumor.

26. The method of claim 24, wherein the liposome comprises an antineoplastic agent.

27. The method of claim 26, wherein the antineoplastic agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methyl-prednisone, and navalbene.

28. The method of claim 24, wherein the administration of (a) comprises intravenous administration.

29. The method of claim 24, wherein the acyl groups of the phospholipid are saturated.

30. The method of claim 24, wherein the phospholipid and lysolipid are contained in a molar ratio of from 99:1 to 50:50.

31. The method of claim 30, wherein the lysolipid is monopalmitoylphosphatidylcholine (MPPC), monolaurylphosphatidylcholine (MLPC), monomyristoylphosphatidylcholine (MMPC), monostearoylphosphatidylcholine (MSPC), and mixtures thereof.

32. The method of claim 24, wherein the active agent is entrapped within the interior of the liposome.

33. The method of claim 24, wherein the active agent is entrapped within the gel-phase lipid bilayer membrane of the liposome.

34. The method of claim 24, wherein the liposome has a diameter of from about 50 nanometers to about 400 nanometers.

35. The method of claim 24, wherein the gel-phase lipid bilayer membrane further comprises a phospholipid derivatized with a hydrophilic polymer.

36. The method of claim 35, wherein the hydrophilic polymer is selected from the group consisting of polyethylene glycol, polylactic acid, polyglycolic acid, copolymers of polylactic acid and polyglycolic acid, polyvinyl alcohols, polyvinylpyrrolidone, oligosaccharides, and mixtures thereof.

37. The method of claim 24, wherein the active agent is a pharmacologically active agent selected from the group consisting of anesthetics, antihistamines, antineoplastics, anti-ulceratives, anti-seizure agents, muscle relaxants, immunosuppressive agents, anti-infective agents, non-steroidal anti-inflammatory agents, imaging agents, nutritional agents, and mixtures thereof.

38. The method of claim 37, wherein the active agent is selected from the group consisting of antineoplastic agents, non-steroidal anti-inflammatory agents, immunosuppressive agents, and anti-infective agents.

39. The method of claim 37, wherein the active agent is an antihistamine.

40. The method of claim 37, wherein the active agent is a non-steroidal anti-inflammatory agent.

41. The method of claim 40, wherein the active agent is ibuprofen.

42. A pharmaceutical composition comprising a pharmaceutically acceptable diluent or carrier, and a liposome having a gel-phase lipid bilayer membrane having a phase transition temperature, and an active agent,
wherein the gel-phase lipid bilayer membrane comprises:
(a) one or more phospholipids selected from the group consisting of phosphatidyl cholines, phosphatidyl glycerols, phosphatidyl inositols, and phosphatidyl ethanolamines, wherein the one or more phospholipids have two acyl groups; and
(b) one or more lysolipids selected from the group consisting of monoacylphosphatidylcholines, monoacylphosphatidylglycerols monoacylphosphatidylinositols and monacylphosphatidylethanolamines, wherein the one or more lysolipids have one acyl group; and
wherein the active agent is selected from the group consisting of a pharmacologically active agent or a diagnostic agent; and
wherein the phase transition temperature is 39 to 45° C.; and
wherein the amount of the one or lysolipids in the gel-phase lipid bilayer membrane is sufficient to increase a first percentage of active agent released from the liposome at the phase transition temperature, compared to a second percentage of active agent released in the absence of one or more lysolipids.

43. The pharmaceutical composition of claim 42, wherein the liposomes are dispersed in an aqueous preparation.

44. The pharmaceutical composition of claim 43, comprising physiological saline or PBS.

45. The pharmaceutical composition of claim 42, wherein the phospholipid and lysolipid are contained in a molar ratio of from 99:1 to 51:49.

46. The pharmaceutical composition of claim 42, wherein the phospholipid and lysolipid are contained in a molar ratio of from 99:1 to 70:30.

47. The pharmaceutical composition of claim 42, wherein the acyl groups of the phospholipids are saturated.

48. The pharmaceutical composition of claim 42, wherein the lysolipid is monopalmitoylphosphatidylcholine (MPPC), monolaurylphosphatidylcholine (MLPC), monomyristoylphosphatidylcholine (MMPC), monostearoylphosphatidylcholine (MSPC), and mixtures thereof.

49. The pharmaceutical composition of claim 48, wherein the lysolipid is monostearoylphosphatidylcholine (MSPC).

50. The pharmaceutical composition of claim 49, wherein the lysolipid is monostearoylphosphatidylcholine (MSPC) and the phospholipid is dipalmitoylphosphatidylcholine (DPPC).

51. The pharmaceutical composition of claim 48, wherein the lysolipid is monopalmitoylphosphatidylcholine (MPPC) and the phospholipid is dipalmitoylphosphatidylcholine (DPPC).

52. The pharmaceutical composition of claim 42, wherein the active agent is entrapped within the interior of the liposome.

53. The pharmaceutical composition of claim 42, wherein the active agent is entrapped within the gel-phase lipid bilayer membrane.

54. The pharmaceutical composition of claim 42, wherein the liposome has a diameter of from about 50 nanometers to about 400 nanometers.

55. The pharmaceutical composition of claim 42, wherein the gel-phase lipid bilayer further comprises a phospholipid derivatized with a hydrophilic polymer.

56. The pharmaceutical composition of claim 53, wherein the hydrophilic polymer is selected from the group consisting of polyethylene glycol, polylactic acid, polyglycolic acid, copolymers of polylactic acid and polyglycolic acid, polyvinyl alcohols, polyvinylpyrrolidone, oligosaccharides, and mixtures thereof.

57. The pharmaceutical composition of claim 42, wherein the active agent is a pharmacologically active agent selected from the group consisting of anesthetics, antihistamines, antineoplastics, anti-ulceratives, anti-seizure agents, muscle relaxants, immunosuppressive agents, anti-infective agents, non-steroidal anti-inflammatory agents, imaging agents, nutritional agents, and mixtures thereof.

58. The pharmaceutical composition of claim 57, wherein the active agent is selected from the group consisting of antineoplastic agents, non-steroidal anti-inflammatory agents, immunosuppressive agents, and anti-infective agents.

59. The pharmaceutical composition of claim 57, wherein the active agent is an antihistamine.

60. The pharmaceutical composition of claim 57, wherein the active agent is an antineoplastic agent or antitumor agent.

61. The pharmaceutical composition of claim 60, wherein the active agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methylprednisone, and navalbene.

62. The pharmaceutical composition of claim 61, wherein the active agent is paclitaxel.

63. The pharmaceutical composition of claim 61, wherein the active agent is camptothecin.

64. The pharmaceutical composition of claim 61, wherein the active agent is doxorubicin.

65. The pharmaceutical composition of claim 57, wherein the active agent is a non-steroidal anti-inflammatory agent.

66. The pharmaceutical composition of claim 65, wherein the active agent is ibuprofen.

67. The liposome of claim 1, wherein the one or more phospholipids have two C16–C24 acyl groups.

68. The liposome of claim 1, wherein the one or more lysolipids have one C18–C22 acyl group.

* * * * *